United States Patent
Younis et al.

(10) Patent No.: US 7,085,342 B2
(45) Date of Patent: Aug. 1, 2006

(54) METHOD FOR TRACKING MOTION PHASE OF AN OBJECT FOR CORRECTING ORGAN MOTION ARTIFACTS IN X-RAY CT SYSTEMS

(75) Inventors: Waheed Younis, Toronto (CA); Storgios Stergiopoulos, Toronto (CA)

(73) Assignee: Canamet Canadian National Medical Technologies Inc, Toronto (CA)

( * ) Notice: Subject to any disclaimer, the term of this patent is extended or adjusted under 35 U.S.C. 154(b) by 98 days.

(21) Appl. No.: 10/829,185

(22) Filed: Apr. 22, 2004

(65) Prior Publication Data

US 2005/0238135 A1 Oct. 27, 2005

(51) Int. Cl.
*G01N 23/00* (2006.01)

(52) U.S. Cl. .............................. 378/8; 378/4
(58) Field of Classification Search .................. 378/4, 378/8, 15, 19, 901
See application file for complete search history.

(56) References Cited

U.S. PATENT DOCUMENTS

| | | | |
|---|---|---|---|
| 5,251,128 A | 10/1993 | Crawford | |
| 5,671,263 A | 9/1997 | Ching-Ming | |
| 6,236,705 B1 * | 5/2001 | Stergiopoulos et al. | 378/8 |
| 6,421,552 B1 | 7/2002 | Hsieh | |
| 6,535,570 B1 * | 3/2003 | Stergiopoulos et al. | 378/8 |
| 2004/0081270 A1 * | 4/2004 | Heuscher | 378/4 |
| 2004/0082846 A1 * | 4/2004 | Johnson et al. | 600/410 |

OTHER PUBLICATIONS

Bresler et al., "*Optimal interpolation in helical scan 3D computerized tomography*", Proc Int Conference Acoustics Speech Signal Processing, vol. 3, pp. 1472-1475, 1989.

Brink et al., "*Helical CT: Principles and Technical Considerations*", Radio Graphics, vol. 14, No. 4, pp. 887-893, Jul. 1994.

Chiu et al., "*Tomographic Reconstruction of Time-Varying Object from Linear Time-Sequential Sampled Projections*", Proc. IEEE Conf. ASSP, Adelaide, 1, pp. V309-V312, 1994.

Crawford et al., "*Respiratory Compensation in Projection Imaging using a Magnification and Displacement Model*", IEEE TMI, 15(3), pp. 327-332. 1996.

(Continued)

*Primary Examiner*—David V. Bruce
*Assistant Examiner*—Hoon Song
(74) *Attorney, Agent, or Firm*—Freedman & Associates

(57) ABSTRACT

The present invention relates to a method for tracking motion phase of an object. A plurality of projection data indicative of a cross-sectional image of the object is received. The projection data are processed for determining motion projection data of the object indicative of motion of the object based on the attenuation along at least a same line through the object at different time instances. A motion phase of the object with the object having the least motion is selected. Finally, projection data acquired at time instances within the selected motion phase of the object are selected for tomographical image reconstruction. Reconstructed images clearly show a substantial improvement in image quality by successfully removing motion artifacts using the method for tracking motion phase of an object according to the invention. The method is highly beneficial in cardiac imaging using X-ray CT scan.

36 Claims, 20 Drawing Sheets

OTHER PUBLICATIONS

Dhanantwari et al., "*Correcting Organ Motion Artifacts in X-Ray CT Medical Imaging Systems by Adaptive Processing (Part I: Theory)*", Medical Physics J., 28 (8), pp. 1562-1576, Aug. 2001.

Dhanantwari et al., "*Correcting Organ Motion Artifacts in X-ray CT Systems Based on Tracking of Motion Phase by the Spatial Overlap Correlator (Part II: Experimental Study)*", Medical Physics J., 28 (8), pp. 1577-1596, Aug. 2001.

Kalender et al., "*Spiral volumetric CT with single-breath-hold technique, continuous transport, and continuous scanner rotation*", Radiology, vol. 176, pp. 967-982, 1990.

Morehouse et al., "*Gated Cardiac Computed Tomography with a Motion Phantom*", Radiol., 134(1), pp. 213-217, 1980.

Ritchie et al., "*Predictive Respiratory Gating: A New Method to Reduce Motion Artifacts in CT scans*", Radiology, 190, pp. 847-852, 1994.

Sayed et al., "*A State-Space Approach to Adaptive RLS Filtering*", IEEE SP Mag. pp. 18-60, Jul. 1994.

Shepp et al., "*The Fourier Reconstruction of a Head Section*", IEEE Trans. Nucl. Sci., vol. NS-21, pp. 21-43, 1974.

Stergiopoulos, "*Optimum Bearing Resolution for a Moving Towed Array and Extension of its Physical Aperture*", JASA, 87(5), pp. 2128-2140, 1990.

Stergiopoulos, "*Implementation of Adaptive and Synthetic-Aperture Processing Schemes in Integrated Active-Passive Sonar Systems*", Proc IEEE, 86(2), pp. 358-396, Feb. 1998.

Urban et al., "*Detection of focal hepatic lesions with spiral CT: comparison of 4- and 8-mm inter-scan spacing*". AJR 160, pp. 783-785, 1993.

Wang et al., "*A Knowledge-based Cone-beam x-ray CT algorithm for Dynamic Volumetric Cardiac Imaging*", Medical Physics, 29(8), pp. 1807-1822, Aug. 2002.

\* cited by examiner

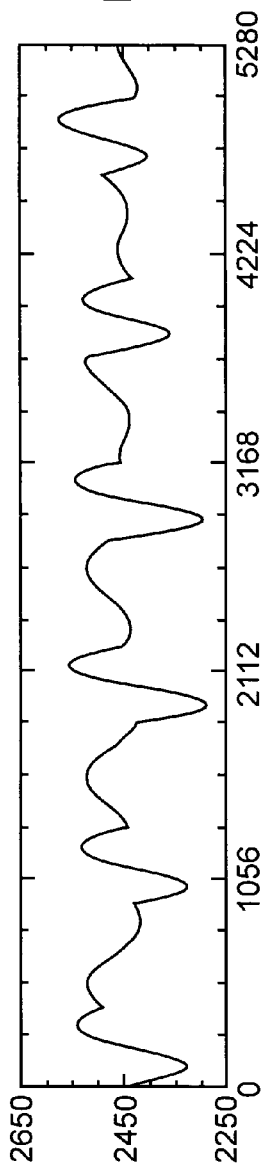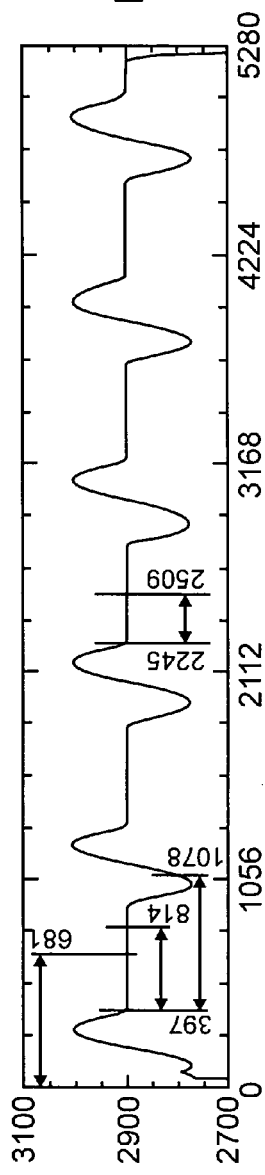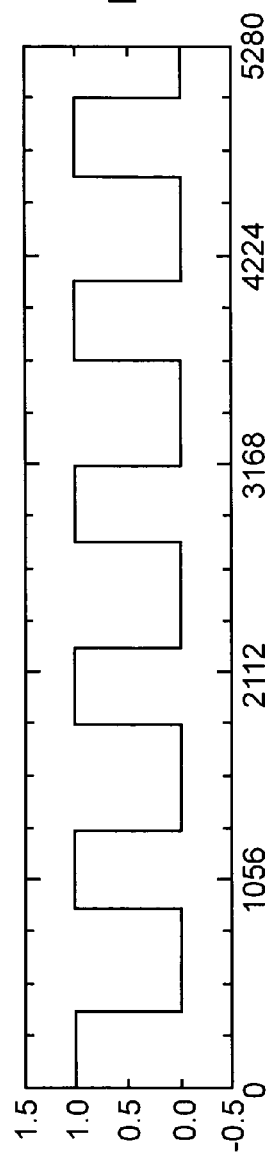

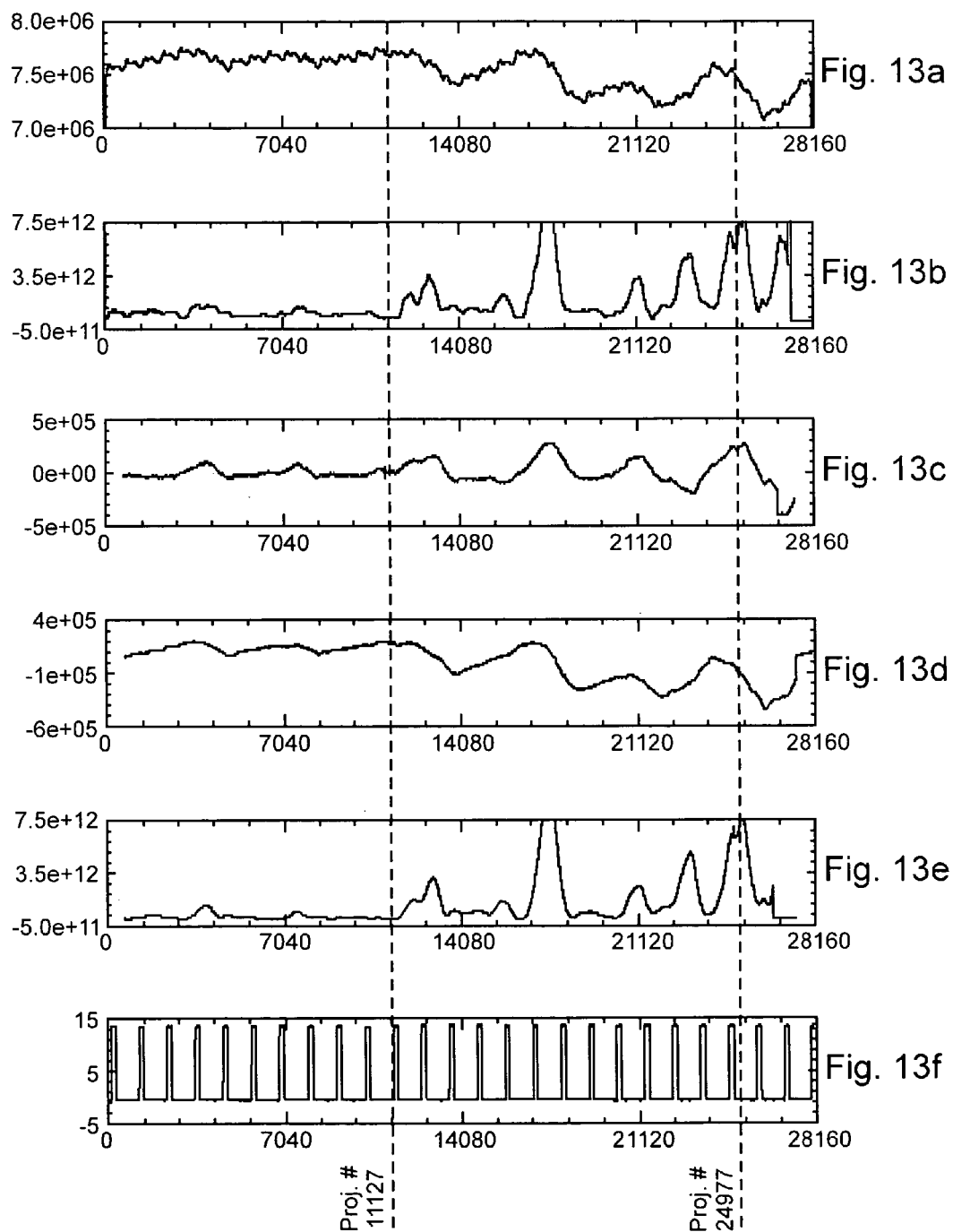

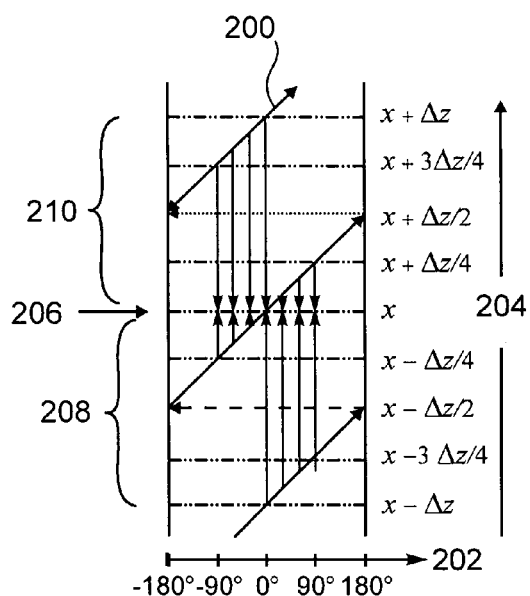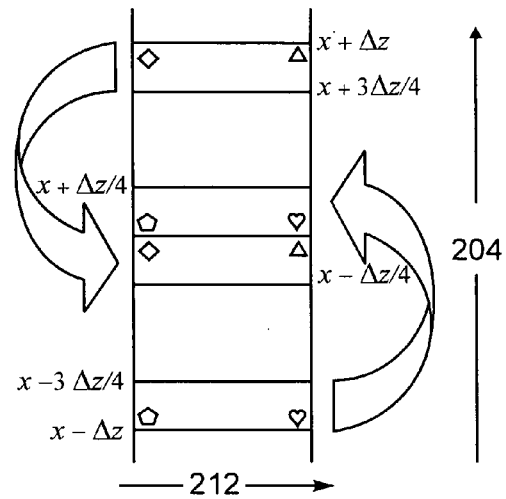
Fig. 18a
Fig. 18b
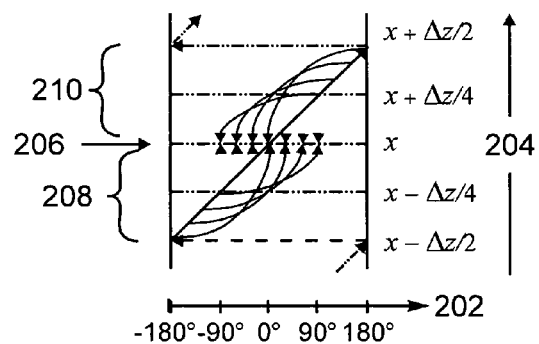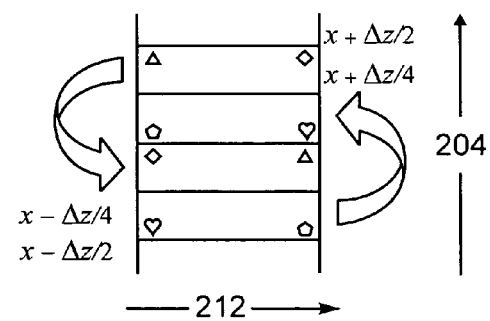
Fig. 19a
Fig. 19b

METHOD FOR TRACKING MOTION PHASE OF AN OBJECT FOR CORRECTING ORGAN MOTION ARTIFACTS IN X-RAY CT SYSTEMS

FIELD OF THE INVENTION

This invention relates to medical imaging and in particular to signal processing methods correcting organ motion artifacts in cardiac imaging.

BACKGROUND OF THE INVENTION

X-ray Computed Tomography (CT) is a medical imaging tool providing cross-sectional images or images of "slices" of a human body. A patient is placed between an X-ray source and an array of detectors for measuring the amount of radiation passing through the patient's body. During the data acquisition process, the source and the detectors are rotated around the patient acquiring a large number of X-ray projection data. The X-ray projection data are then processed using a tomographic image reconstruction process in order to produce an image of a cross-section of the patient's body. For the data acquisition and the image reconstruction process it is assumed that the object—patient's organs— being scanned is stationary. This assumption is violated when there is any motion such as cardiac motion, blood flow, respiratory motion, or patient restlessness during the relatively long period of data acquisition, which is between 0.5 and 2.5 seconds for third generation X-ray CT scanners. The violation of this assumption causes motion artifacts, which appear as blurring, doubling and/or streaking in the reconstructed image. As is evident, such artifacts substantially impede diagnosis or even lead to erroneous diagnosis.

Several techniques for removing these artifacts have been disclosed in the prior art. For example, Crawford, C. R., King, K. F., Ritchie, C. J., and Godwin, J. D.: "*Respiratory Compensation in Projection Imaging using a Magnification and Displacement Model*", IEEE TMI, 15(3), pp. 327–332, 1996, teach a linear model for the motion, while Ritchie, C. J., Hsieh, J., Gard, M. F., Godwin, J. D., Kim., Y, and Crawford, C. R.: "*Predictive Respiratory Gating. A New Method to Reduce Motion Artifacts in CT Scans*", Radiology, 190, pp. 847–852, 1994, model the motion as periodic and take projection data at a particular point in the motion cycle, producing a stroboscope-like effect. However, the organ motion is much more complex and these techniques have a severely limited ability for correcting organ motion. In a more general technique disclosed by Chiu, Y. H., and Yau, S. F.: "*Tomographic Reconstruction of Time-Varying Object from Linear Time-Sequential Sampled Projections*", Proc. IEEE Conf. ASSP, Adelaide, 1, pp. V309–V312, 1994, motion effects are iteratively suppressed from the projection data. This process requires proper initialization in order to achieve an acceptable convergence period. Another technique based on retrospective gating is taught by Morehouse, C. C., Brody, W. R., Guthaner, D. F., Breiman, R. S., and Harell, G. S.: "*Gated Cardiac Computed Tomography with a Motion Phantom*", Radiol., 134(1), pp. 213–217, 1980, and employs an ECG signal to identify the diastole phase of a patient's cardiac cycle—i.e. when the heart is least active—and use the projection data collected during the diastole phase to reconstruct the tomographic image.

Although the correction methods disclosed in the above cited references reduce the adverse effects of motion to some extent, none of these methods substantially removes the motion artifacts from the reconstructed tomographic images.

SUMMARY OF THE INVENTION

It is, therefore, an object of the invention to provide a method and system for processing X-ray CT projection data to track organ motion.

It is further an object of the invention to substantially improve image quality of tomographic images by substantially removing motion artifacts.

It is yet further an object of the invention to provide a method for processing X-ray CT projection data for correcting organ motion artifacts for cardiac imaging.

In accordance with the present invention there is provided a method for tracking motion phase of an object comprising:

receiving a plurality of projection data indicative of at least a cross-sectional image of the object, the projection data being in dependence upon a detector signal indicative of attenuation of an X-ray beam along a line through the object between an X-ray source and a detector, the projection data being acquired such that the projection data are in dependence upon the attenuation along different lines through the object and in dependence upon the attenuation along same lines through the object at different time instances;

processing the projection data for determining motion projection data of the object indicative of motion of the object based on the attenuation along at least a same line through the object at different time instances;

selecting a motion phase of the object from the motion projection data; and, selecting the projection data acquired at time instances within the selected motion phase of the object.

In accordance with the present invention there is provided a method for tracking motion phase of an object comprising the steps for:

receiving a plurality of projection data indicative of at least a cross-sectional image of the object, the projection data being in dependence upon a detector signal indicative of attenuation of an X-ray beam along a line through the object between an X-ray source and a detector, the projection data being acquired such that the projection data are in dependence upon the attenuation along different lines through the object and in dependence upon the attenuation along same lines through the object at different time instances;

processing the projection data for determining motion projection data of the object indicative of motion of the object based on the attenuation along at least a same line through the object at different time instances;

selecting a motion phase of the object from the motion projection data; and, selecting the projection data acquired at time instances within the selected motion phase of the object.

In accordance with the present invention there is further provided a method for tracking motion phase of an object comprising:

providing an X-ray source and at least a detector;

using the at least a detector sensing X-ray beam radiation attenuated by the object along a line through the object between the X-ray source and the detector and providing projection data in dependence thereupon;

rotating the X-ray source and at least a detector around the object for acquiring projection data in dependence upon the attenuation of the X-ray beam along different lines through the object;

rotating the X-ray source and at least a detector around the object a plurality of times for acquiring projection data in dependence upon the attenuation of the X-ray beam along same lines at different time instances;
processing the projection data for determining motion projection data of the object indicative of motion of the object based on the attenuation along at least a same line through the object at different time instances;
selecting a motion phase of the object from the motion projection data; and,
selecting the projection data acquired at time instances within the selected motion phase of the object.

In accordance with the present invention there is further provided a method for tracking motion phase of an object comprising the steps for:
providing an X-ray source and at least a detector;
using the at least a detector sensing X-ray beam radiation attenuated by the object along a line through the object between the X-ray source and the detector and providing projection data in dependence thereupon;
rotating the X-ray source and at least a detector around the object for acquiring projection data in dependence upon the attenuation of the X-ray beam along different lines through the object;
rotating the X-ray source and at least a detector around the object a plurality of times for acquiring projection data in dependence upon the attenuation of the X-ray beam along same lines at different time instances;
processing the projection data for determining motion projection data of the object indicative of motion of the object based on the attenuation along at least a same line through the object at different time instances;
selecting a motion phase of the object from the motion projection data; and,
selecting the projection data acquired at time instances within the selected motion phase of the object.

In accordance with the present invention there is yet further provided a storage medium having stored therein executable commands for execution on a processor, the processor when executing the commands performing:
receiving a plurality of projection data indicative of at least a cross-sectional image of the object, the projection data being in dependence upon a detector signal indicative of attenuation of an X-ray beam along a line through the object between an X-ray source and a detector, the projection data being acquired such that the projection data are in dependence upon the attenuation along different lines through the object and in dependence upon the attenuation along same lines through the object at different time instances;
processing the projection data for determining motion projection data of the object indicative of motion of the object based on the attenuation along at least a same line through the object at different time instances;
selecting a motion phase of the object from the motion projection data; and,
selecting the projection data acquired at time instances within the selected motion phase of the object.

Reconstructed tomographical images clearly show a substantial improvement in image quality by successfully removing motion artifacts using the method for tracking motion phase of an object according to the invention. Employment of the method for tracking motion phase of an object according to the invention is highly beneficial in cardiac imaging using X-ray CT scan. The method is easily implemented as retrofit into existing X-ray CT scanners including helical X-ray CT scanners, for example, as executable commands provided on a storage medium for execution on an existing signal processing system.

BRIEF DESCRIPTION OF THE FIGURES

Exemplary embodiments of the invention will now be described in conjunction with the following drawings, in which:

FIGS. 12a to 12c are diagrams illustrating the processing of projection data using a second embodiment of the method for tracking motion phases of an object according to the invention;

FIGS. 13a to 13f are diagrams illustrating the processing of projection data of a first patient using the first and the second embodiment of a method for tracking motion phases of an object according to the invention;

FIG. 18a is a diagram illustrating 360° interpolation of helical projection data;

FIG. 18b is a diagram illustrating a sinogram corresponding to FIG. 18a;

FIG. 19a is a diagram illustrating 180° interpolation of helical projection data;

FIG. 19b is a diagram illustrating a sinogram corresponding to FIG. 19a;

DETAILED DESCRIPTION OF THE INVENTION

In X-ray CT, projection data is processed using a tomographic image reconstruction process producing a cross-sectional image of a patient's body. For the data acquisition and the image reconstruction process it is assumed that the object—patient's organs—being scanned is stationary. This assumption is violated when there is any motion such as cardiac motion, blood flow, respiratory motion, or patient restlessness during the relatively long period of data acquisition, which is between 0.5 and 2.5 seconds for third generation X-ray CT scanners. In particular, motion artifacts caused by cardiac motion substantially impede diagnosis or even lead to erroneous diagnosis in cardiac imaging.

In order to overcome this problem and to enable use of X-ray CT scanners in cardiac imaging, a method for tracking motion phase of an object according to the invention has been implemented into the processing of the X-ray CT projection data. During a cardiac cycle speed of heart motion is not uniform. Within a fraction of the cardiac cycle—diastole phase—the heart is less active, i.e. there is less motion, compared to the rest of the cardiac cycle. The method for tracking motion phase of an object according to the invention, which will be described in detail below, identifies the projection data that have been acquired during the "less active"—diastolic—phase of the cardiac cycle. Once these projection data are correctly identified they are fed into the tomographic image reconstruction process producing images substantially free of cardiac motion artifacts. As will become evident to those skilled in the art, the method for tracking motion phase of an object according to the invention is not limited for tracking cardiac motion, but is also applicable for tracking phase of other types of motion.

In order to provide better understanding of the method for tracking motion phase of an object according to the invention, the acquisition of the projection data in X-ray CT scanners and the process of tomographic image reconstruction from the projection data will be briefly discussed in the following.

Figure 1:
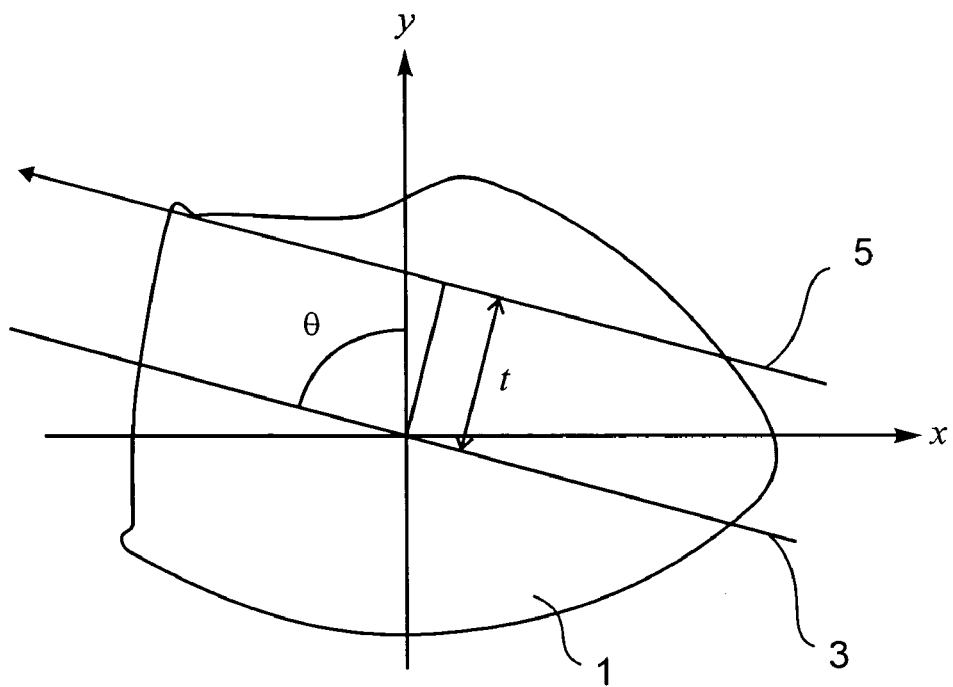
FIG. 1 is a simplified diagram schematically illustrating parallel beam projection in an X-ray CT scanner.

When an X-ray beam 5 passes through an object 1, as shown in FIG. 1, which is modeled as a two dimensional distribution f(x, y) of the X-ray attenuation, total attenuation suffered by the X-ray beam is determined as the line integral of the attenuation along the straight line 5, which is given by:

$$x \cos\theta + y \sin\theta = t,$$

with respect to reference line 3. The total attenuation is then given by:

$$P(\theta, t) = \int_{-\infty}^{\infty}\int_{-\infty}^{\infty} f(x, y)\delta(x\cos\theta + y\sin\theta - t)\,dx\,dy.$$

Figure 2:
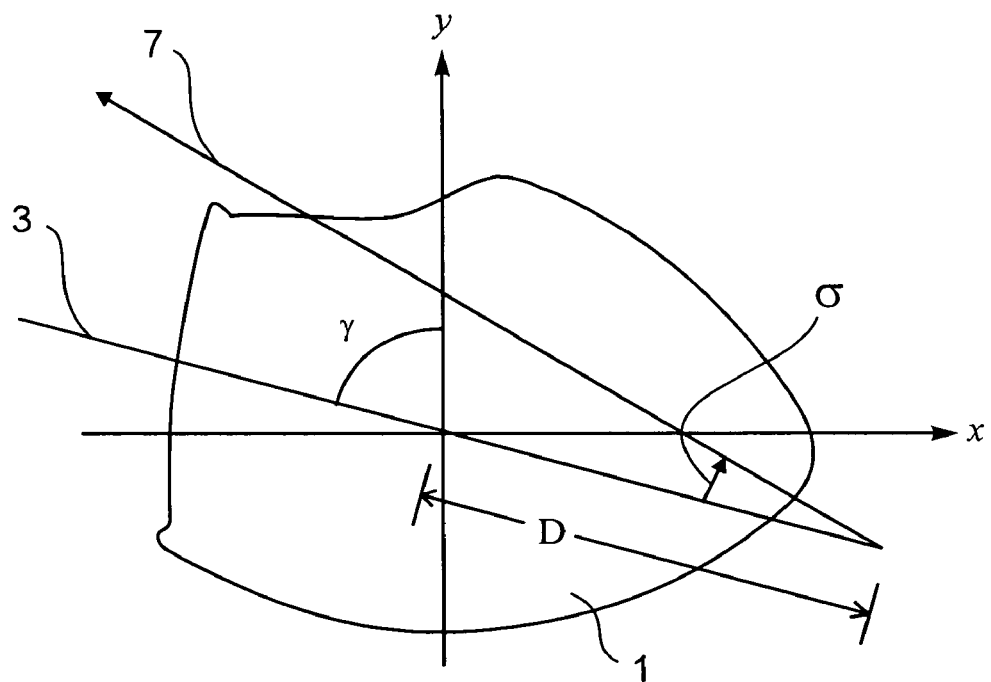
FIG. 2 is a simplified diagram schematically illustrating fan beam projection in an X-ray CT scanner.

Here, $\delta(\ldots)$ is the Dirac delta function and $P(\theta, t)$ is known as Radon Transform of the function f(x, y). A projection is formed by combining a set of these line integrals. The simplest projection is a collection of parallel line integrals as is given by $P(\theta, t)$ for a constant $\theta$ and varying t—parallel projection. In another type of projection known as fan beam projection, the line integrals are determined along fan lines, as shown in FIG. 2, given by:

$$x \cos(\gamma+\sigma) + y \sin(\gamma+\sigma) = D \sin\sigma.$$

The line integrals are then given by:

$$R(\gamma, \sigma) = \int_{-\infty}^{\infty}\int_{-\infty}^{\infty} f(x, y)\delta(x\cos(\gamma+\sigma) + y\sin(\gamma+\sigma) - D\sin\sigma)\,dx\,dy.$$

In third generation CT scanners utilizing fan beam projection, the data acquisition process is performed using discrete detectors. These discrete projection measurements $R(\gamma_n, \sigma_m)$, (n=1,2, ..., N), (m=1,2, ..., M) are the line integrals given by:

$$R(\gamma_n, \sigma_m) = \int\int f(x, y)\delta(x \cos(\gamma_n+\sigma_m) + y \sin(\gamma_n+\sigma_m) - D \sin\sigma_m)\,dx\,dy,$$

where the projection angle is $\gamma_n$, and the m-th detector within the detector array is oriented at an angle $\sigma_m$ with respect to the center of the array. The angular step increment between two successive projections is defined by: $\Delta\gamma = 2\pi/N$, $\Delta t$ is the time elapsed between two successive projections and N is the total number of projections acquired during the period $T = N\Delta t$ required for one full rotation of the source and detector array around the object f(x, y) being scanned.

For the tomographic image reconstruction Fourier Slice Theorem or, more frequently, filtered back projection is applied. For fan beam projection data a modified version of the filtered back projection—known as weighted filtered back projection—is used.

The tomographic image reconstruction process of an image f(x, y) from the parallel projections $P(\theta, t)$ is briefly outlined as follows:

$$f(x, y) = \frac{1}{2}\int_0^{2\pi} Q(\theta, x\cos\theta + y\sin\theta)\,d\theta, \tag{1}$$

where $$Q(\theta, t) = \int_{-\infty}^{\infty} S(\theta, w)|w|e^{j2\pi wt}\,dw, \tag{2}$$

with $S(\theta, w)$ being the Fourier transform of the projection $P(\theta, t)$:

$$S(\theta, w) = \int_{-\infty}^{\infty} P(\theta, t)e^{-j2\pi wt}\,dt.$$

Equations (2) and (1) represent the operations of filtering and back projection, respectively, hence the name filtered back projection. Details concerning filtered back projection, weighted filtered back projection as well as computer implementations of the same are disclosed in Kak, A. C. and Slaney, M.: "*Principles of Computerized Tomographic Imaging*", New York, IEEE Press, 1999.

Figure 3:
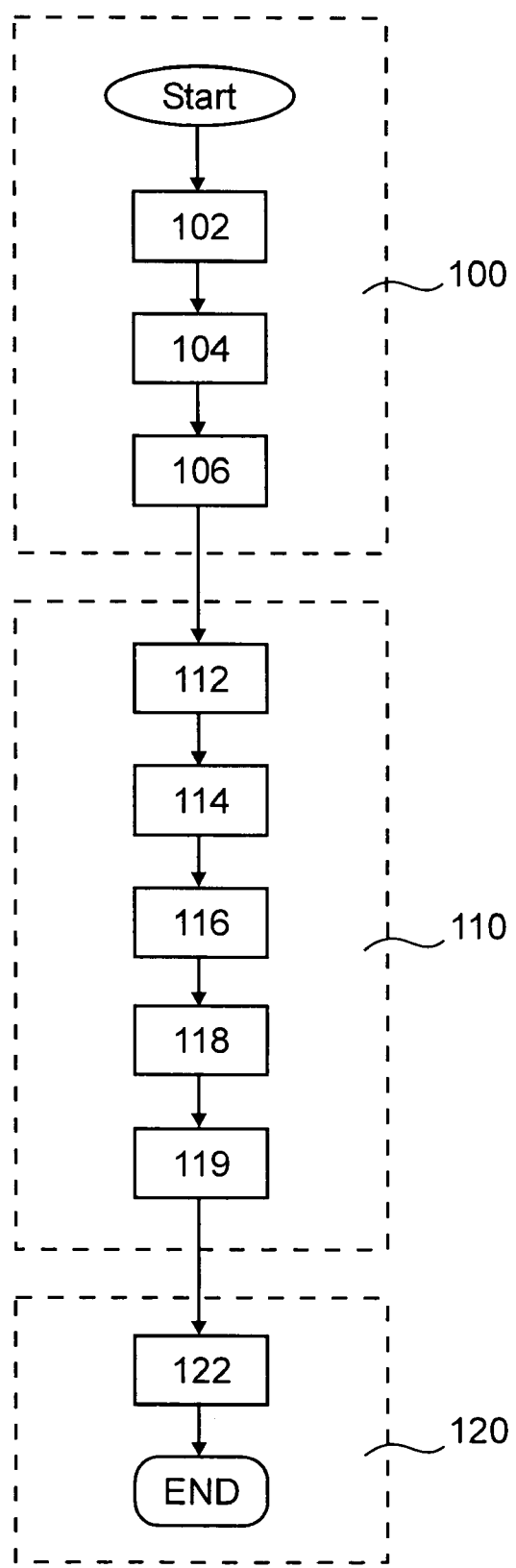
FIG. 3 is a simplified flow diagram illustrating processing of projection data employing a method for tracking motion phases of an object according to the invention.

Referring to FIG. 3, a simplified flow diagram of the method for tracking motion phase of an object according to the invention implemented into an X-ray CT data acquisition and image reconstruction process is shown. An X-ray source and at least a detector of an X-ray CT scanner 100 are rotated around the object—box 102. The detector senses the X-ray beam radiation attenuated by the object along a line through the object between the X-ray source and the detector—box 104—and provides projection data in dependence thereupon—box 106. During one full rotation of the X-ray source and the detector projection data in dependence upon the attenuation of the X-ray beam along different lines in a cross-sectional plane through the object are acquired. By rotating the X-ray source and the detector several times around the object, projection data in dependence upon the attenuation of the X-ray beam along same lines at different time instances are acquired. Using a processor 110 the received projection data—box 112—are processed according to the invention to determine the motion phase of the object with the object having the least motion. The projection data in dependence upon the attenuation of the X-ray beam along same lines through the object acquired at different time instances are compared—box 114—and based on changes of the attenuation—indicating motion of the object—the motion phase of the object corresponding to the least changes of the attenuation is determined—box 116. The projection data acquired at time instances within the determined motion phase of the object are then selected for image reconstruction—box 118. Determination of the motion phase and selection of the corresponding data is performed, for example, by a user on a graphical display of the processed data, or using a processor for comparing the processed data with a threshold. The selected projection data are then processed for tomographic image reconstruction using, for example, filtered back projection—box 120—providing image data indicative of a cross-sectional image of the object, which are then displayed—box 122—using, for example a monitor 120.

In the following, two embodiments of the method for tracking motion phase of an object according to the invention, as indicated above in boxes 114 to 118, will now be described in more detail. In the first embodiment a Spatial Overlap Correlator (SOC) is combined with an unwrapping filter for tracking the cardiac motion and accurately detecting the less active phase therefrom. The SOC concept has been described in detail by the present inventor in Stergiopoulos, S.: "*Otpimum Bearing Resolution for a Moving Towed Array and Extension of its Physical Aperture*", JASA, 87(5), pp. 2128–2140, 1990, and in Stergiopoulos, S.: "*Implementation of Adaptive and Synthetic Aperture Processing in Real-Time Sonar Systems*", Proc IEEE, 86(2), pp. 358–396, 1998. The process of SOC is best understood by a simple example. Consider two photographs taken at time instances $t_0$ and $t_0+\Delta t$ of a field of view including a moving train and stationary objects such as trees and houses. If corresponding pixels of the two photographs are subtracted from each other, the resulting image includes only information about the motion of the train during $\Delta t$. In a similar fashion, projection data acquired at different time instances $t_0$ and $t_0+\Delta t$ but along same lines through the object are compared to detect motion of the object during $\Delta t$.

Consider a fixed detector $m_0$ in the detector array of an X-ray CT scanner. The detector is rotated p times around a given stationary object and acquires projection data x[n]. The projection data x[n] when plotted versus time n is a periodic signal with period N, which is the total number of projections during a full rotation around the object. It is noted that x[n] is zero outside the interval $0 \leq n < pN$. A circularly shifted version $x_s[n]$ of x[n] is defined as follows:

$$x_s[n] = \begin{cases} x[n+N] & \text{for } 0 \leq n < (p-1)N \\ x[n-(p-1)N] & \text{for } (p-1)N \leq n < pN \end{cases} \quad (3)$$

Figure 4A:
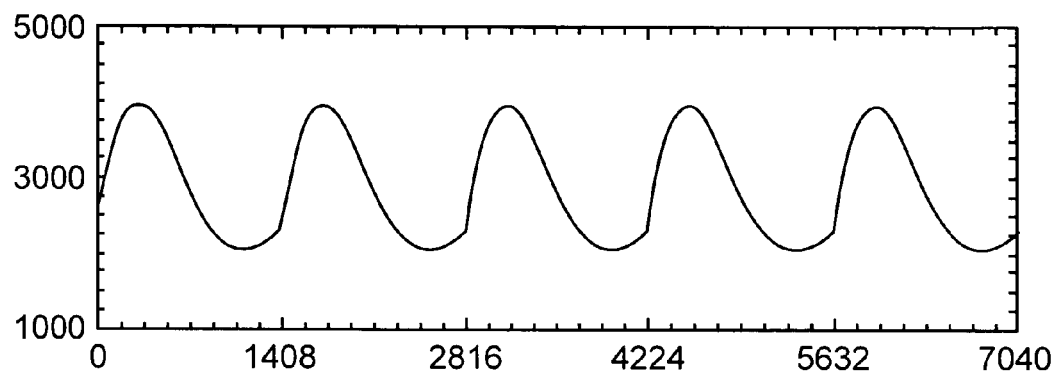
FIGS. 4a to 4c are diagrams illustrating simulated projection data for a stationary object.
Figure 4B:
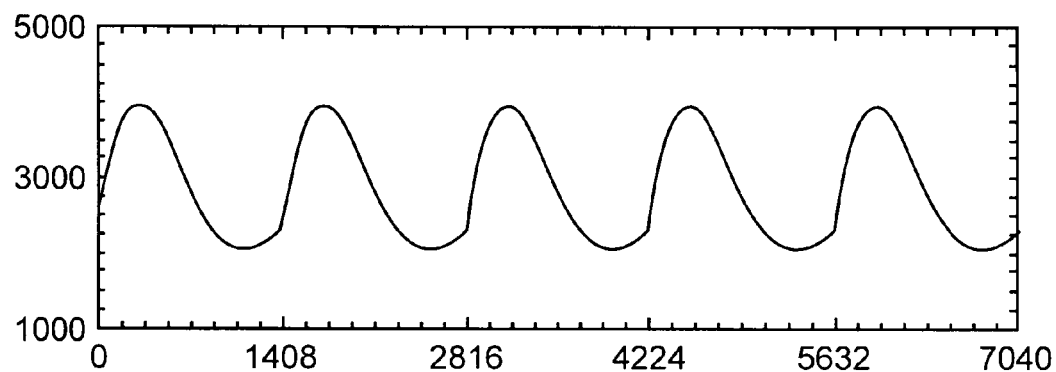

In other words, the projection data x[n] have been shifted to the left by one period N and wrapped around the first period at the end on the right, as shown in FIG. 4a—projection data x[n]—and 4b—circularly shifted version $x_s[n]$—for simulated projection data for a stationary object with the number of rotations p=5 and the number of projections per rotation N=1408. Since x[n] is periodic with period N it is not possible to detect a difference between x[n] and $x_s[n]$. SOC of x[n] is defined as:

$$x_{SOC}[n] = x[n] - x_s[n]. \quad (4)$$

Figure 4C:
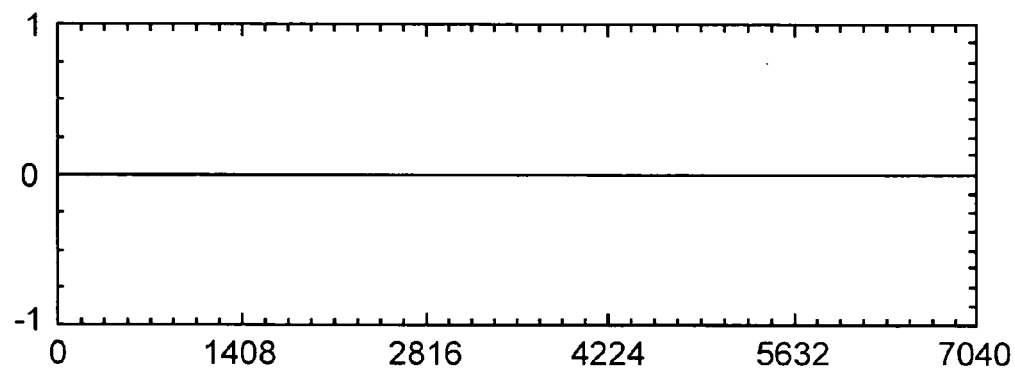

For a given stationary object this signal is zero for all n, as shown in FIG. 4c. For a given projection $n=n_0$, the two signal values $x[n_0]$ and $x_s[n_0]$ represent the line integral of the given object along a same line but at different times. This is because the X-ray source and the detector $m_0$ are disposed at same physical locations at both time instances. If the object is stationary the measurements are identical.

Now considering the case when a weaker signal y[n] is superimposed on x[n] generating a new signal $$z[n] = x[n] + y[n]. \quad (4)$$

Figure 5A:
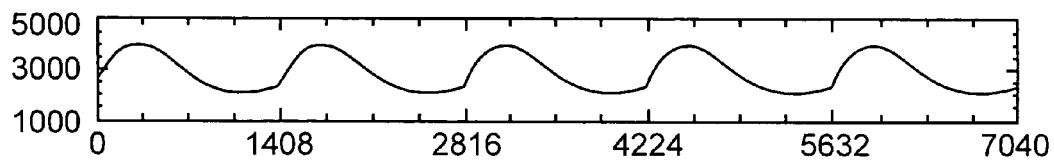
FIGS. 5a to 5f are diagrams illustrating the processing of projection data using a first embodiment of a method for tracking motion phases of an object according to the invention.
Figure 5B:
Figure 5C:
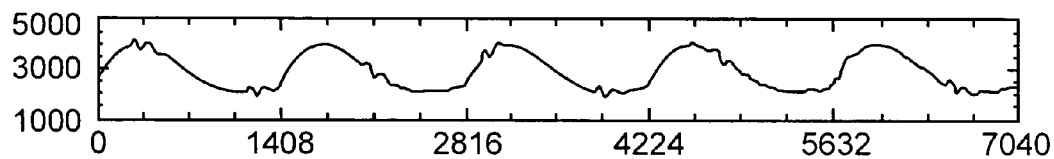
Figure 5D:
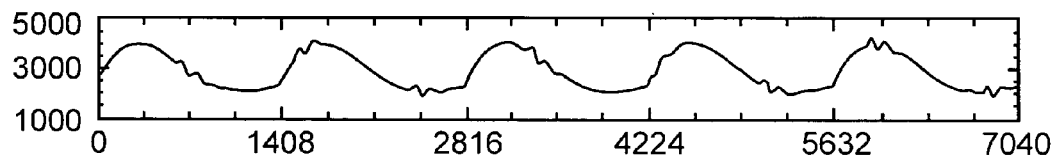

FIG. 5a illustrates an X-ray CT projection signal x[n] observed by a detector scanning a patient with no motion. It is periodic with a period equivalent to a full rotation—1408 projections per second. FIG. 5b is a heartbeat signal y[n] with 95 beats per minute. FIG. 5c illustrates a projection signal z[n] observed by the detector when scanning the patient with heartbeat. The goal is to recover the signal y[n] from the observed projection signal z[n] —FIG. 5c. In order to recover the heartbeat signal y[n] from the observed projection signal z[n], the observed projection signal z[n] is first circularly shifted by one period N resulting in $z_s[n]$, shown is FIG. 5d. Then the SOC of the observed signal z[n] is determined as $$z_{SOC}[n] = z[n] - z_s[n] = x[n] + y[n] - x_s[n] - y_s[n]$$
$$= x[n] - x_s[n] + y[n] - y_s[n] = y[n] - y_s[n].$$

The reason for the term $y[n]-y_s[n]$ not to disappear is because it is not periodic with the period N. Taking the SOC of the observed signal z[n] cancels the portion of z[n] with period N—x[n]—and leaves the portion that is not periodic with period N—the term $y[n]-y_s[n]$, shown in FIG. 5e. In other words, the stationary signal components have been removed leaving only the signal portions due to the moving/deforming object. However, due to the circular shifting of the observed signal and wrapping of the first period, information about a time reference is lost in the signal shown in FIG. 5e. In the following steps the lost time information is recovered by obtaining y[n] from y[n]−y$_s$[n]. Considering pN point Fast Fourier Transforms (FFTs) of y[n], y$_s$[n], and y[n]−y$_s$[n] as follows:

$$y[n] \overset{FFT}{\longleftrightarrow} Y[k] = \sum_{n=0}^{pN-1} x[n] e^{-j\left(\frac{2\pi}{pN}\right)kn} \text{ for } k = 0, 1, \ldots, pN-1$$

$$y_s[n] \overset{FFT}{\longleftrightarrow} Y[k] e^{j\left(\frac{2\pi}{pN}\right)kN}$$

$$z_{SOC}[n] = y[n] - y_s[n] \overset{FFT}{\longleftrightarrow} Z_{SOC}[k] = Y[k]\left(1 - e^{-j\left(\frac{2\pi}{p}\right)k}\right).$$

Now it is possible to recover y[n] from $z_{SOC}[n] = y[n] - y_s[n]$ as:

$$y[n] \overset{FFT}{\longleftrightarrow} Y[k] = \frac{Z_{SOC}[k]}{\left(1 - e^{-j\left(\frac{2\pi}{p}\right)k}\right)} \quad (6)$$

$$= \frac{Z_{SOC}[k]}{\left(1 - \cos\left(\frac{2\pi k}{p}\right)\right) + j \sin\left(\frac{2\pi k}{p}\right)}.$$

Figure 5E:
Figure 5F:
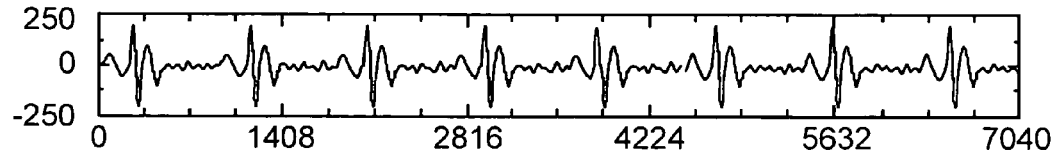

Using the relation in equation (6) the lost information about a time reference in the signal shown in FIG. 5e is recovered resulting in the heartbeat signal y[n] shown in FIG. 5f. A comparison with the signal shown in FIG. 5b indicates that the heartbeat motion phases have been correctly recovered.

It is noted that the denominator in equation (6) becomes zero whenever k/p is an integer—which will happen N times. In order to avoid "dividing-by-zero", the denominator is set to be $$\varepsilon + j \sin\left(\frac{2\pi k}{p}\right)$$

when $$1 - \cos\left(\frac{2\pi k}{p}\right) \leq \varepsilon.$$

Figure 6:
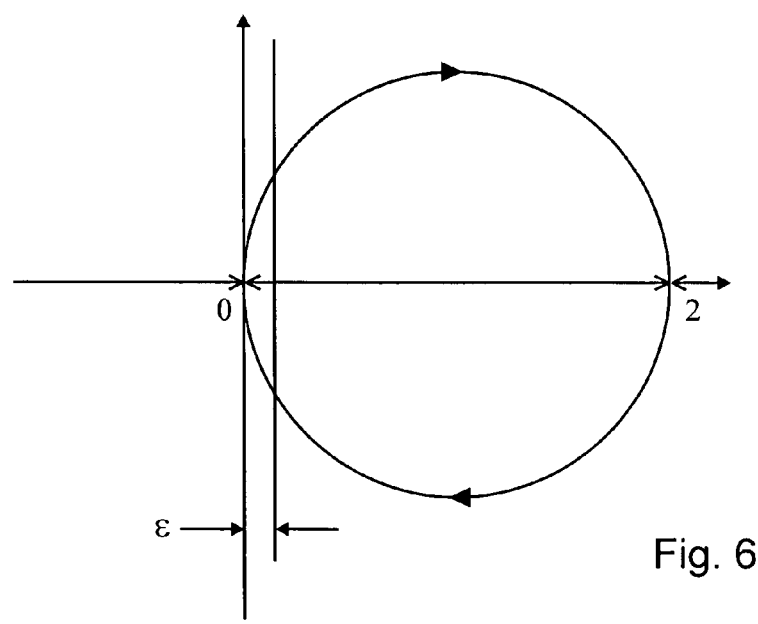
FIG. 6 is a simplified diagram illustrating geometrically operation of an unwrapping filter according to the invention in the first embodiment.

It is interesting to note that the denominator of equation (6) represents geometrically traversing a circle at discrete points exactly N times, as shown in FIG. 6. Further, if the amount of shift to produce z$_s$[n] is one half the total length of z[n]—i.e. p=2 in the current setting—the denominator of equation (6) reduces to 1−(−1)$^k$—i.e. 0,2,0,2,0, . . . for k=0,1,2,3,4, . . . respectively. This corresponds to the two points indicated by "x" in FIG. 6 and simply scales down the FFT of z$_{SOC}$[n]. Consequently, it is not possible to recover y[n] from y[n]−y[n] in this case.

While in the above example z$_s$[n] was generated by shifting z[n] equivalent to one rotation—i.e. N projections—it is possible to shift z[n] by half rotation N/2 in case of a middle detector of a detector array, because the middle detector measures the line integral along a same line after every half rotation—i.e. the signal detected by the middle detector is periodic with period N/2. For other detectors of the detector array it is possible to determine half rotation SOC by processing the projection data obtained from the detector array—parallel beam sinogram data—using the symmetry property of the Radon transform. This results in a significantly lesser amount of projection data to be acquired exposing a patient to a lesser amount of radiation.

The processing according to equation (6) is referred to herein as an "unwrapping filter" as it restores the temporal information of y[n], which was lost—or wrapped up—in y[n]−y$_s$[n]. It is noted that though the temporal contents of y[n] are restored, the DC component of y[n] is lost because y[n]−y$_s$[n] is a zero mean signal. In order to account for the effect of shifting and wrapping as defined by y$_s$[n] in equation (3) it is important to apply a corresponding FFT— here pN point FFT—in equation (6).

Summarizing, if a weaker signal y[n] caused by cardiac motion is superimposed on a regular projection signal x[n] due to a stationary object resulting in an observed projection signal z[n], the SOC processing shown above removes the signal component caused by the stationary object. Using the unwrapping filter temporal information lost during the SOC process is recovered allowing identification of the less active phase of the cardiac cycle versus the temporal axis. FIGS. 5c to 5f illustrate the signal processing steps of SOC and unwrapping filter.

In the following, a second embodiment of the method for tracking motion phase of an object according to the invention will be described. Here, the less active phase of the cardiac cycle is identified using a property of the Radon transform. The property will be briefly described before its application for tracking the motion phase of an object is explained.

Let P(θ, t) be the Radon transform of an object f(x, y) contained within a unit circle, which is possible without loss of generality. The integral $$\int_{-1}^{1} P(\theta, t) t^k \, dt$$

is a homogeneous polynomial of degree k in cos θ and sin θ, where k=0,1, . . . i.e.

$$\int_{-1}^{1} P(\theta, t) t^k \, dt = \sum_{j=0}^{k} a_j \cos^{k-j}\theta \sin^j \theta \quad \forall \, k \geq 0 \; (k \text{ integer}).$$

For k=1 follows $$\int_{-1}^{1} P(\theta, t) t \, dt = a_0 \cos\theta + a_1 \sin\theta$$

$$= \sqrt{a_0^2 + a_1^2} \sin\left(\theta + \tan^{-1}\left(\frac{a_0}{a_1}\right)\right).$$

From the above equation follows that the center of mass $$\int_{-1}^{1} P(\theta, t) t \, dt$$

has a sinusoidal dependence on θ. Even in the case of the function f(x, y) consisting of a single point it is mapped to a sinusoid in P(θ, t). Therefore, the function P(θ, t) is called a "sinogram".

For k=0 follows $$\int_{-1}^{1} P(\theta, t) dt = a_0 \text{ (i.e. constant) } \forall \theta \quad (7)$$

The constant on the right hand side of equation (7) is called the "mass of the object" and is a measure of the total X-ray attenuation constant of the object f(x, y). It is evident that the mass of a given object—or the total X-ray attenuation constant—is constant regardless of a projection angle from which it is viewed.

Equation (7) states that the integral of the Radon transform with respect to t is constant for all θ for a given stationary object. The data acquisition process in parallel beam projection results in a 2-D array called "sinogram matrix". The dimensions of this matrix are pN—total number of projections—by M—number of detectors in the detector array. According to the property of equation (7), the sum of this matrix along M results in a constant vector of length pN provided the object was stationary. If the objects starts deforming at some projection, the total X-ray attenuation constant starts changing and as a result the vector will start changing at the same projection. If the vector starts deviating from its constant value at a projection $n_0$ it is an indication of a start of motion of the object at that projection time. Therefore, the motion phase of an object is tracked by integrating the Radon transform of the projection data according to equation (7)—i.e. the sum along M of the sinogram matrix—and tracking the changes of the sum of the sinogram matrix.

It is noted that the above equations are valid for parallel beam projection data and not for fan beam projection data. In order to apply the method for tracking the motion phase of an object as outlined above the fan beam data are re-sorted into equivalent parallel beam data. This process is known as "rebinning" and performed according to the following relationship:

t=D sin σ and θ=γ+σ.

Figure 7:
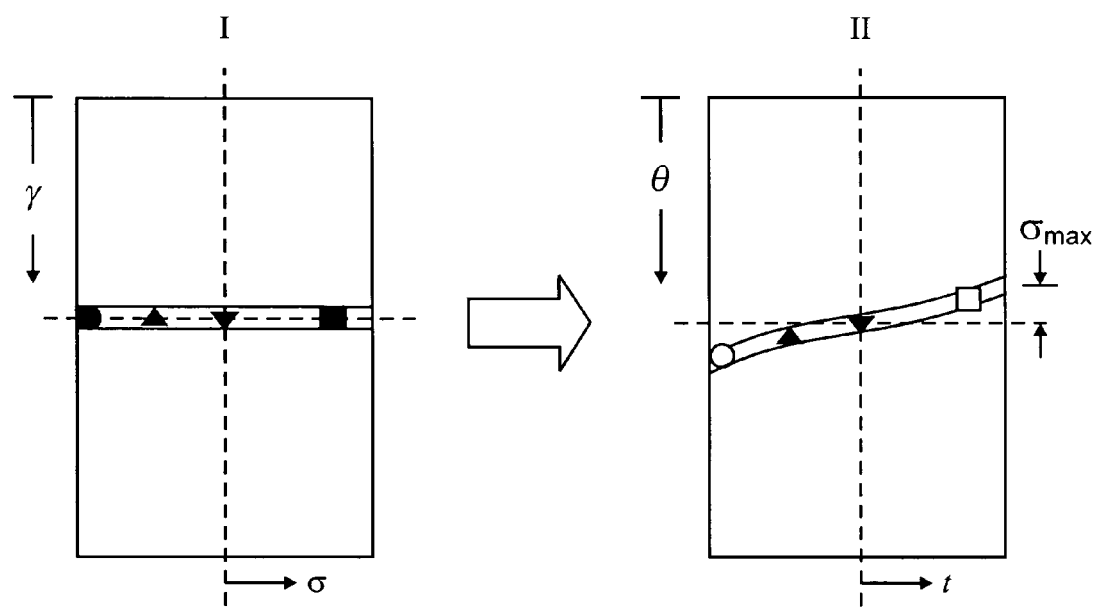
FIG. 7 is a simplified diagram illustrating conversion of fan beam data into parallel beam data.

The parameters of the above relationships are described above and illustrated in FIGS. 1 and 2. The process of rebinning from fan beam data I to parallel beam data II is shown in FIG. 7. The vertical dashed line indicates the location of the central detector. As a result of the rebinning, the data corresponding to a single fan projection is spread over a range equivalent to the fan angle in the corresponding parallel projection. Due to this spread the effect of a starting motion of the object is spread over a range when transformed from fan beam to parallel beam data.

Figure 8:
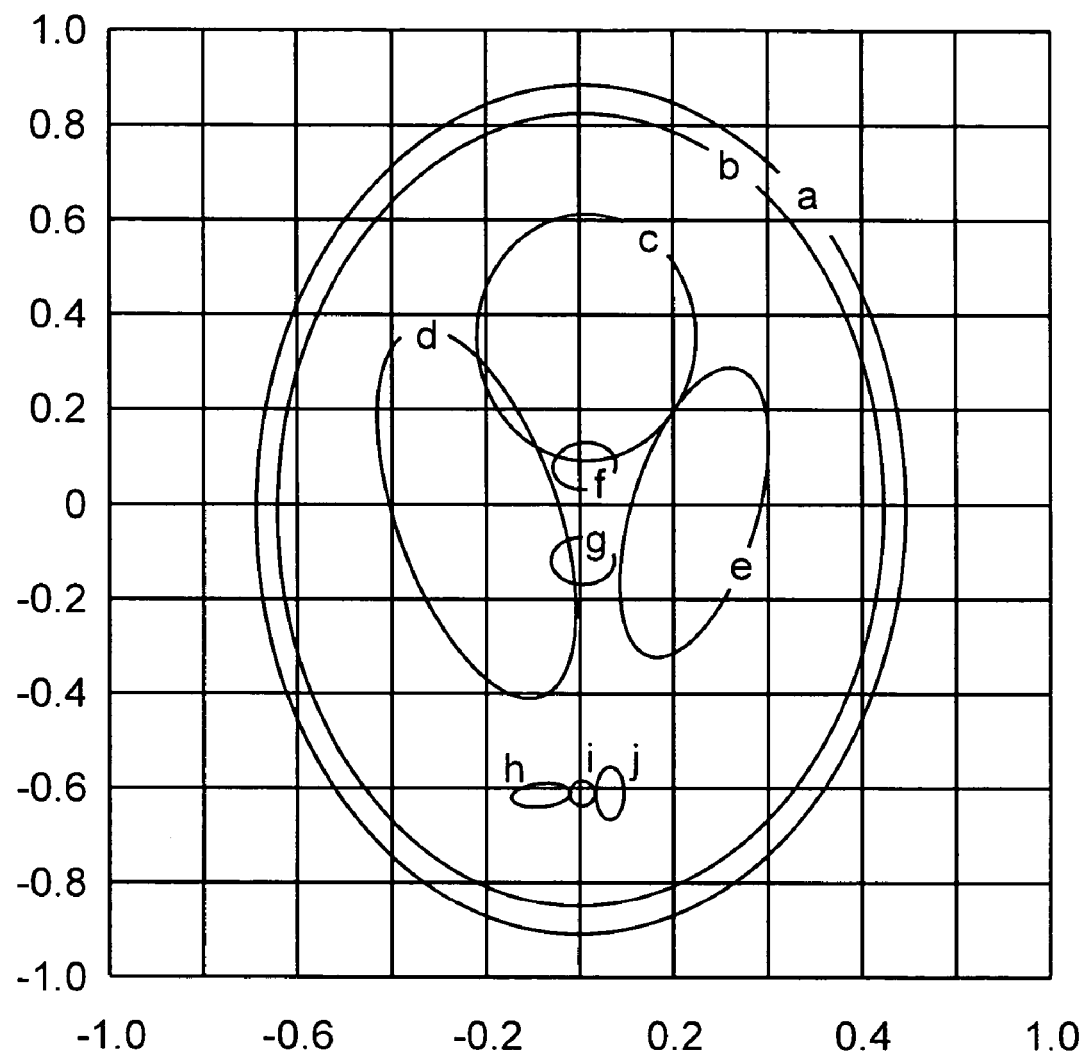
FIG. 8 is a simplified diagram illustrating the Shepp and Logan head phantom.
Figure 9A:
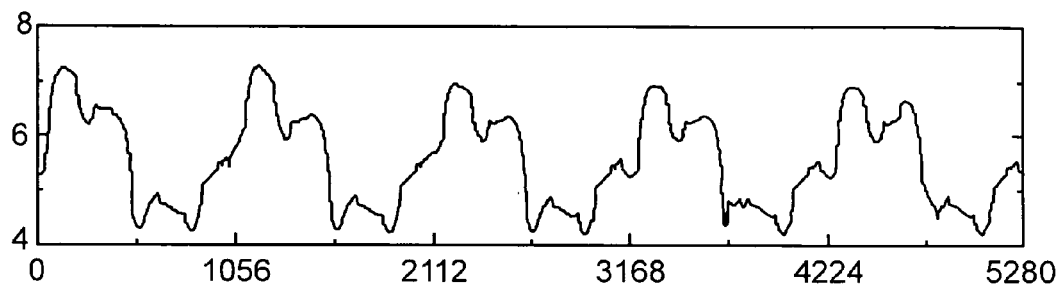
FIGS. 9a to 9d are diagrams illustrating the processing of projection data obtained from single detector measurements using the first embodiment of the method for tracking motion phases of an object according to the invention.
Figure 9B:
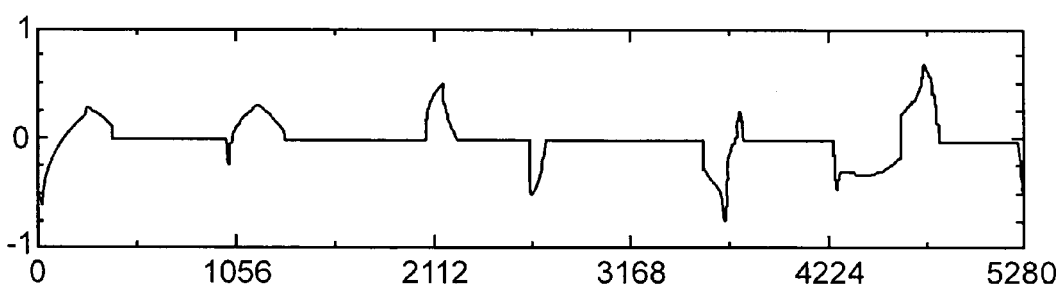
Figure 9C:
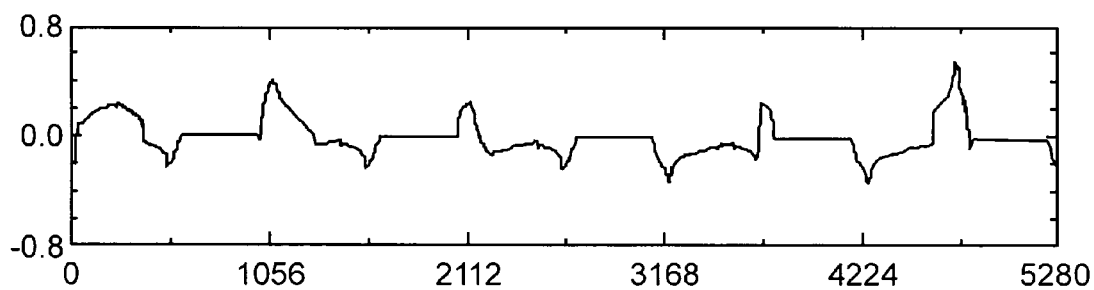
Figure 9D:
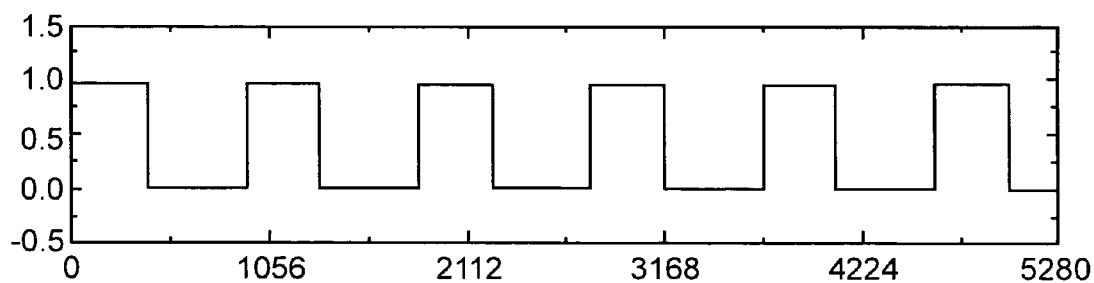

In the following, applications of the method for tracking motion phase of an object according to the invention will be described using simulated data and real patient data. CT scanner projection data for the Shepp and Logan head phantom have been simulated. The phantom comprises 10 ellipses, shown in FIG. 8, with one—ellipse "d"—pulsating for simulating cardiac motion. Projection data for 5 rotations of the CT scanner have been simulated with 1056 projections per rotation. The pulsating ellipse was pulsating with 6 pulses during this time interval with a period equivalent to 924 projections. The cycle of the pulsating movement has been set to 43%, i.e. the ellipse was moving for 43% of the time interval and stationary for 57% of the time interval. Implementation of the SOC technique on the simulated phantom data presented some problems in precisely identifying the stationary period of the pulsating ellipse, shown in FIGS. 9a to 9d. FIG. 9a illustrates the simulated projection data of the pulsating phantom detected by one detector. FIG. 9b is the corresponding SOC projection signal. Comparison of FIGS. 9c and 9d, the SOC projection signal after application of the unwrapping filter and the motion reference signal of the ellipse "d", respectively, illustrates the difficulty in identifying the stationary phase of the phantom in this case. The reason for this inaccuracy is that the line corresponding to an X-ray beam between the source and the detector is not intersecting the pulsating ellipse during the whole rotation of the detector. In other words, the pulsating ellipse is not in the line of view for some source-detector locations during their rotation around the phantom object. Hence, equation (5) did not hold during the whole rotation rendering precise detection of the stationary period of the pulsating ellipse impossible. This problem is easily overcome by ensuring that at any time during the rotation, a source-detector line is intersecting the pulsating ellipse by employing, for example, a plurality of detectors instead of a single one and adding the measurements acquired by all the detectors for each projection and forming a single signal.

Figure 10A:
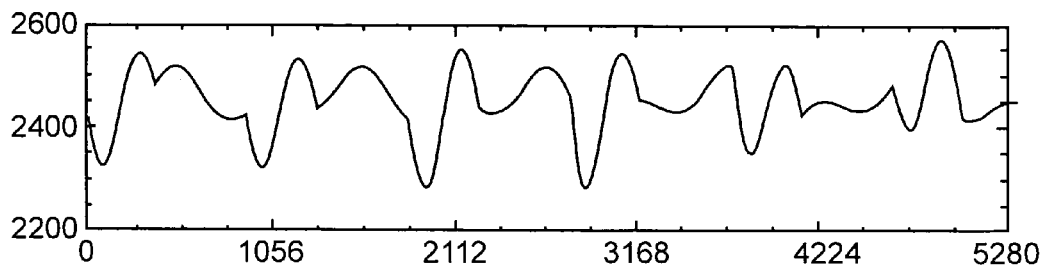
FIGS. 10a to 10d are diagrams illustrating the processing of projection data obtained from sum of detector measurements using the first embodiment of the method for tracking motion phases of an object according to the invention.
Figure 10B:
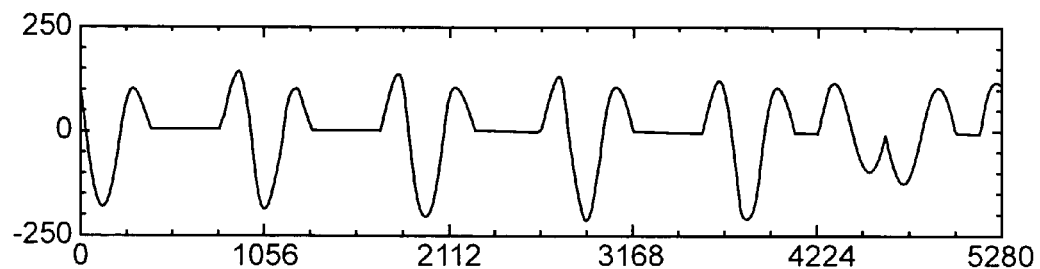
Figure 10C:
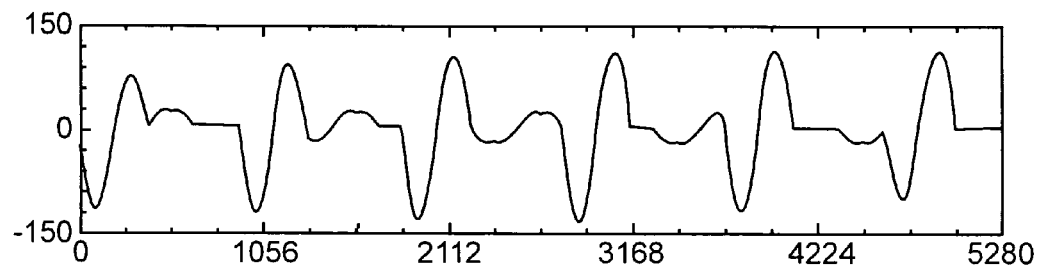
Figure 10D:
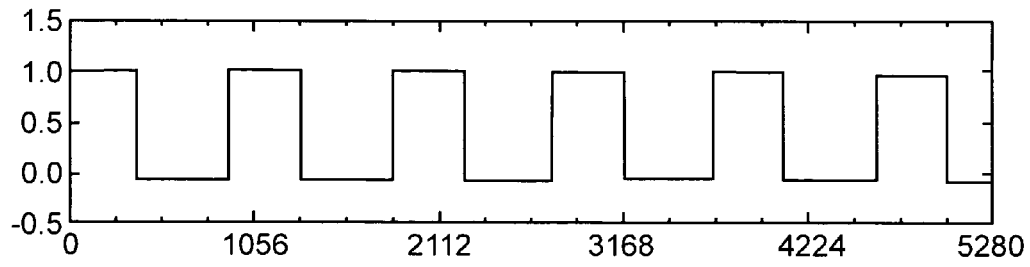
Figure 11A:
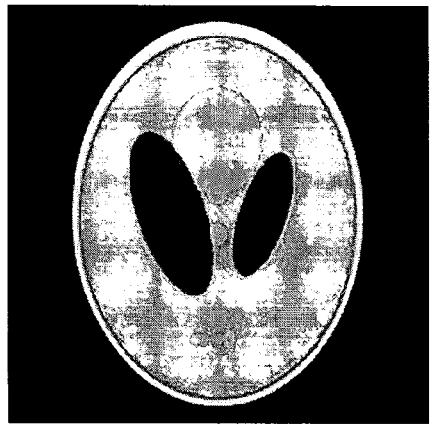
FIGS. 11a to 11d are reconstructed tomographical images.
Figure 11B:
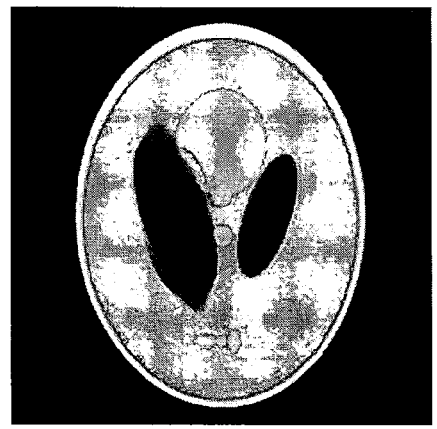
Figure 11C:
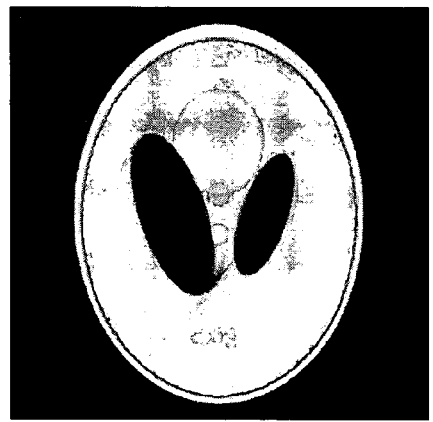

FIGS. 10a to 10d illustrate the simulated projection signals employing the above modified signal processing. In FIG. 10a, the sum of all detector measurements is shown. FIGS. 10b and 10c show the output data from the SOC process and the unwrapping filter, respectively. A comparison of the output data of the unwrapping filter with the actual motion phases of the pulsating ellipse, shown in FIG. 10d, clearly illustrates that the motion phases are precisely identified using the above method for tracking motion phase of an object according to the invention. Finally, FIG. 11a to 11d illustrate reconstructed images based on different portions of the sinogram data. FIG. 11a shows the image of the stationary phantom for comparison. For the current simulation there are 681 projections in 180°+fan angle. Using the projection data obtained in the beginning from projection number 0 to 681 in a standard tomographic image reconstruction without employing the method for tracking motion phase of an object according to the invention will result in an image shown FIG. 11b. Here, motion artifacts due to the pulsating ellipse are clearly visible. Using the motion phase information—FIG. 10c—a single portion of the projection data from projection number 397 to 1078 is selected. As indicated by the signal shown in FIG. 10c there is some motion present. Using these not absolutely motion free data results in the reconstructed image shown in FIG. 11c. Here, some motion artifacts are present but substantially less than in the image shown in FIG. 11b. Finally, two portions of the projection data are selected comprising motion free data—from projection number 397 to 814 and from 2245 to 2509—and used for reconstructing the image shown in FIG. 11d. Comparison with FIG. 11a shows substantial removal of the motion effects of the pulsating ellipse.

Figure 11D:
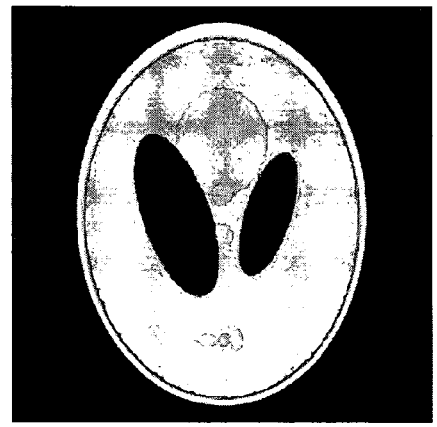

FIGS. 12a to 12c illustrate the processing of fan beam projection signals using the second embodiment of the method for tracking motion phases of an object according to the invention based on the Radon transform property. FIG. 12a shows the sum of detector measurements without rebinning. Converting the fan beam projection data into parallel beam data using rebinning enhance the motion phase information as shown in FIG. 12b. A comparison of the signal shown in FIG. 12b with the actual motion phases of the pulsating ellipse, shown in FIG. 12c, clearly illustrates that the motion phases are precisely identified using the second embodiment of the method for tracking motion phases of an object according to the invention. Selection of projection data-for image reconstruction results in a same image as shown in FIG. 11d. The rebinning process leaves some data points empty in the parallel projection resulting in signal distortions at the beginning and the end of the diagram shown in FIG. 12b. The length of the distortions is half the fan angle at each end. It is obvious that these distortions do not affect the tracking of the motion phases and the projection data selection.

In the following, the method for tracking motion phase of an object has been applied to projection data obtained in clinical tests. For these tests the X-ray CT scanner was positioned to obtain a patient's heart ventricles. The patient was asked to follow breath holding procedures. The CT period of rotation was set to 1.0 second—1408 projections. Projection data were recorded for 20 rotations. For this test, the patient's ECG signal was also recorded. The heart beat was measured to be 75 beats per minute (bpm). In FIG. 13a, the sum of rows of a parallel beam sinogram is shown. Half rotation SOC of the signal in FIG. 13a is shown in FIG. 13c. The result of the unwrapping filter is depicted in FIG. 13d. FIGS. 13a and 13d reveal the motion phase information. In order to more clearly identify the motion phase information, the data shown in FIGS. 13a and 13d are further processed employing a sliding window process step. In FIG. 13b, the standard deviation of a sliding window equivalent to 180°+ fan angle projections—which are 908 projections—is shown, i.e. the value shown at a projection $n_o$ in FIG. 13b is the standard deviation of a window from $n_0$ to $n_0+908$ of FIG. 13a. The same processing has been performed with the data shown in FIG. 13d with the results shown in FIG. 13e. A high value at a projection point in FIGS. 13b and 13e indicates large fluctuations in a data window starting from that point predicting larger motion artifacts in the image reconstructed from the projection data within that window. Accordingly, a small value indicates less fluctuation in the data window predicting an image with lesser motion artifacts. As indicated in FIGS. 13b and 13e, the amplitude of overall movement increases significantly during the latter part of the CT data acquisition process.

Figure 14A:
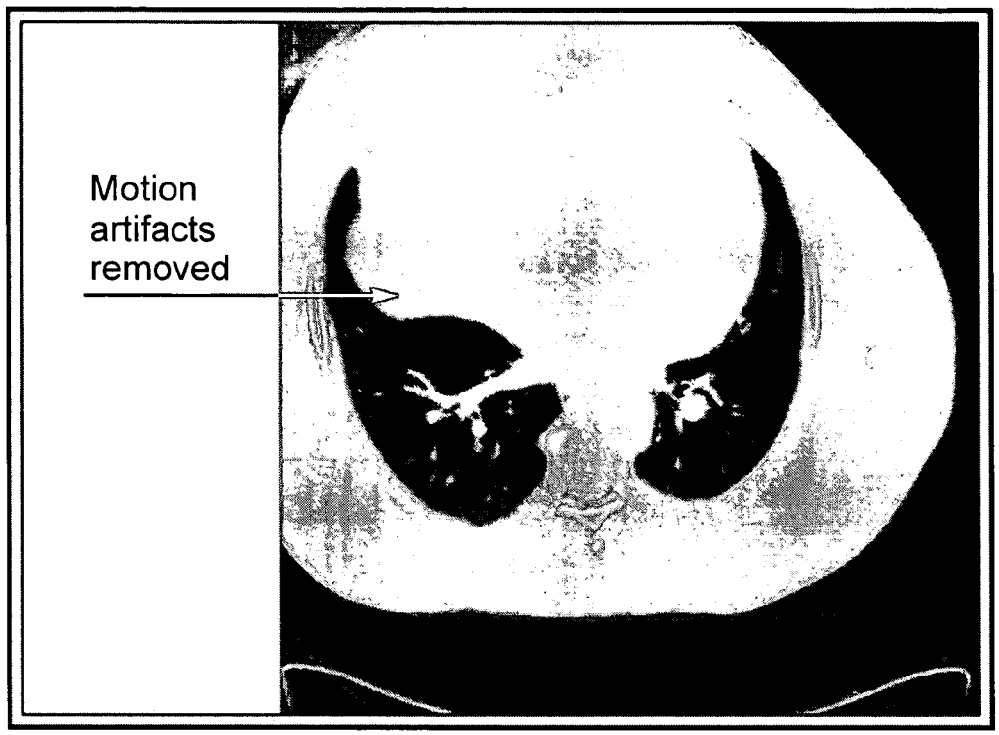
FIGS. 14a and 14b are reconstructed tomographical images.
Figure 14B:
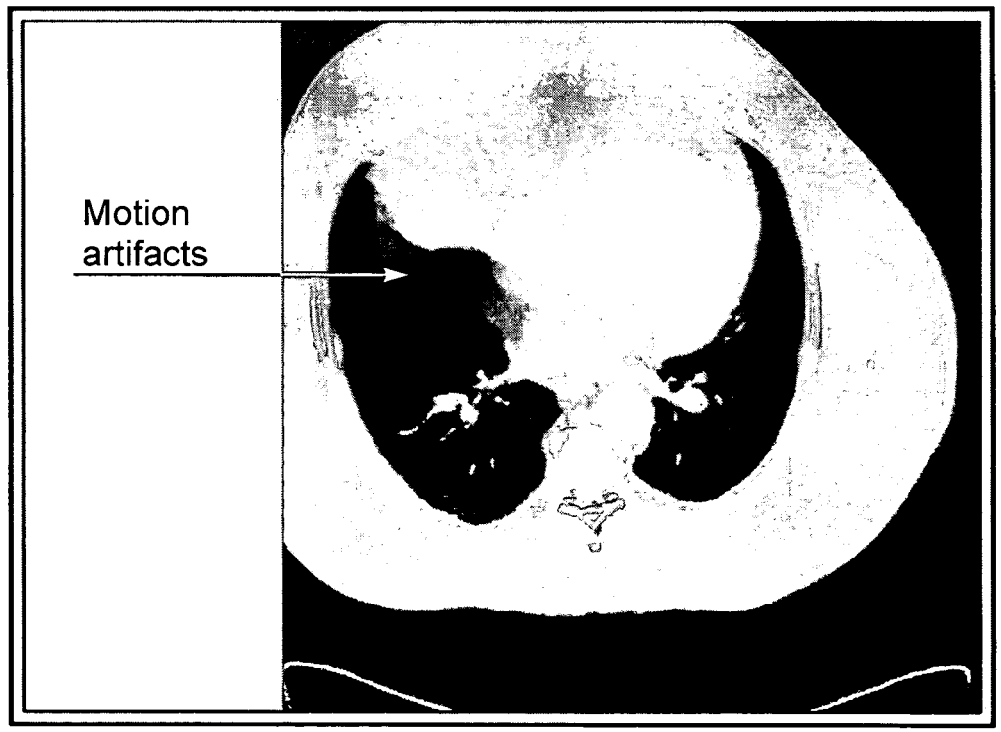

FIG. 13f shows the triggering signal based on the patient's ECG, which is used to implement ECG retrospective gating for identifying phases of cardiac motion. The square pulse of a triggering signal coincides with the QRS peaks of the ECG pulse, which indicates the start of diastole phase when the heart is moving the least. FIGS. 13b and 13d show a low value at projection number 11127—indicated by the first vertical dashed line—indicating lesser motion near the apical portion of the ventricles in a data segment starting at this projection. The image reconstructed from this data segment, shown in FIG. 14a, confirms this, as the heart's pericardium and its thickness in the upper part of the image are clearly visible. Also, the circular lobe of the liver is visible in the left part of the image. According to FIG. 13f, the data segment starting at projection number 11127 includes the QRS phase of the heart cycle suggesting strongest heart motion. This is contrary to the observation using the method according to the invention and FIG. 14a showing least motion artifacts. Another interesting observation is made at projection number 24977—indicated by the second vertical dashed line. Here, the two embodiments of the method according to the invention—FIGS. 13b and 13e—indicate large motion amplitude whereas the ECG signal suggests less motion in a data segment starting from this projection. The image reconstructed from this data segment—FIG. 14b—shows large motion artifacts resulting in an image of substantially inferior quality.

Figure 15A:
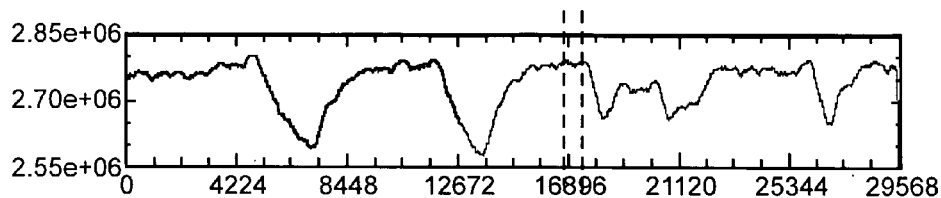
FIGS. 15a to 15e are diagrams illustrating the processing of projection data of a second patient using the first and the second embodiment of a method for tracking motion phases of an object according to the invention.
Figure 15B:
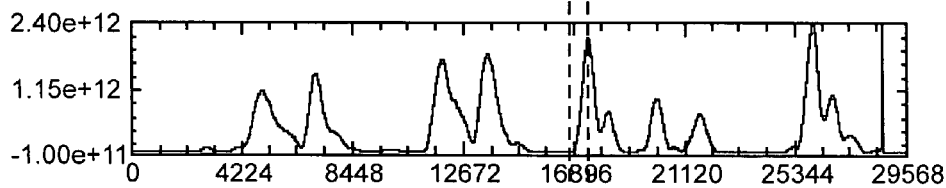
Figure 15C:
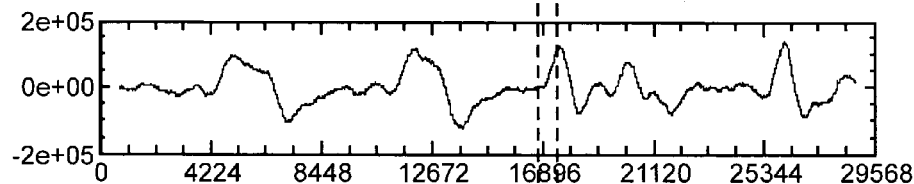
Figure 15D:
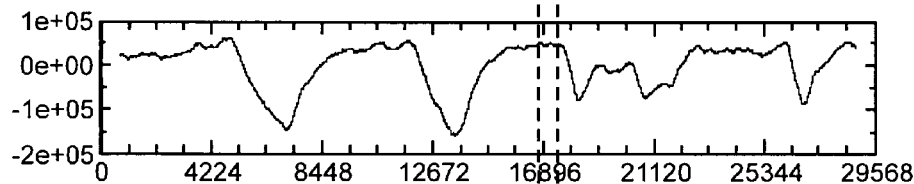
Figure 15E:
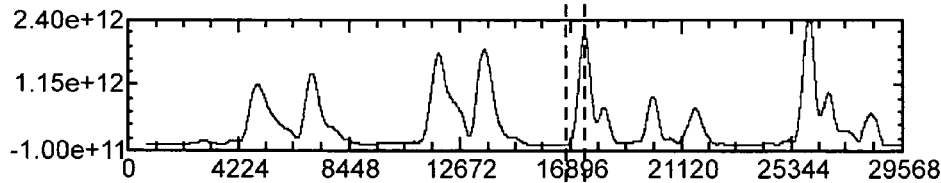
Figure 16A:
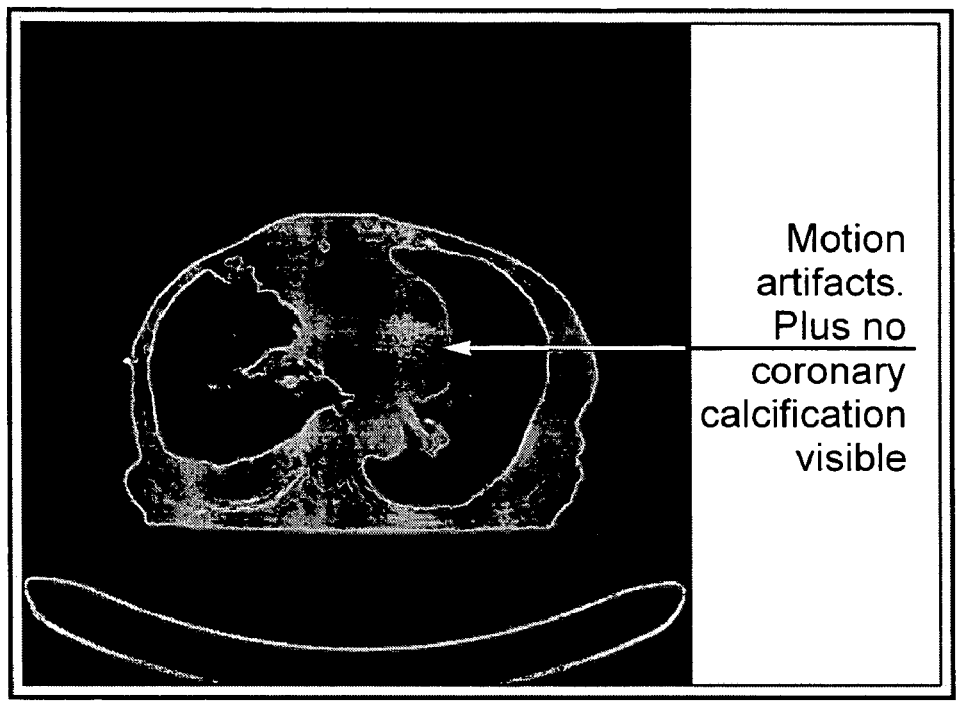
FIGS. 16a and 16b are reconstructed tomographical images.
Figure 16B:
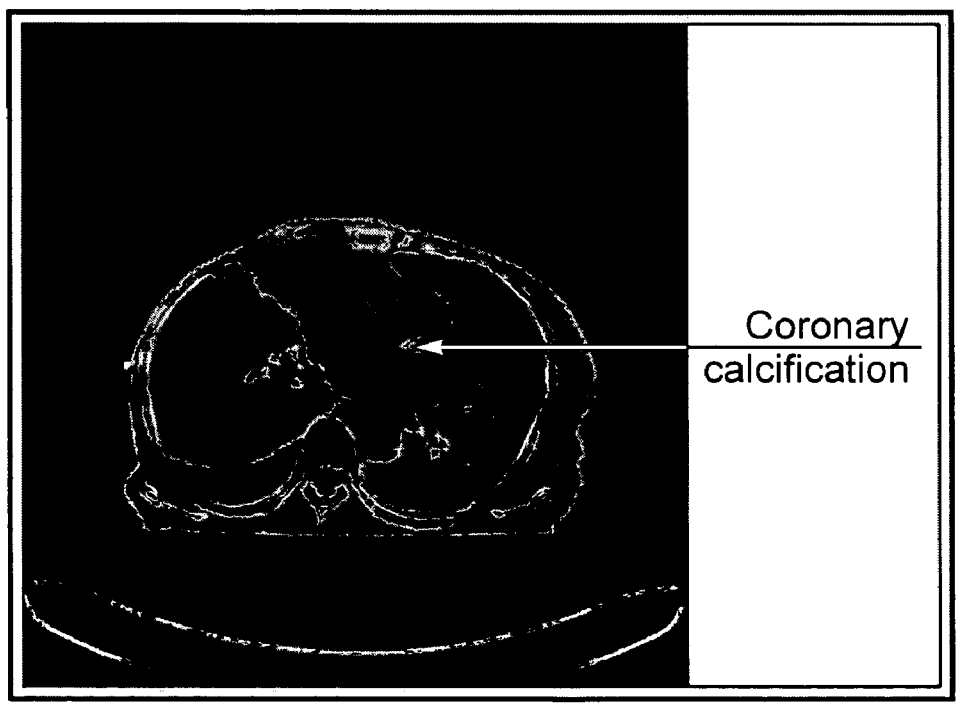

For a second patient, the CT scanner period was again set to 1.0 second—1408 projections—and projection data were recorded for 28 rotations. During the data acquisition process the patient was asked to breathe freely. The patient's heartbeat was recorded to be 72 bpm. The signal processing steps shown in FIGS. 15a to 15e are similar to the ones shown in corresponding FIGS. 13a to 13e. The sum of rows of a parallel projection beam sinogram is shown in FIG. 15a directly providing motion phase information. The output of half rotation SOC and unwrapping filter are shown in FIGS. 15c and 15d, respectively. FIG. 15d also provides motion phase information similar to FIG. 15a. The standard deviation of a sliding window equivalent to 180°+fan angle projections applied to the data shown in FIGS. 15a and 15d are shown in FIGS. 15b and 15e, respectively. From the information given in FIGS. 15b and 15e, two projection points—indicated by vertical dashed lines—have been selected to illustrate the capability of the method for tracking motion phases of an object according to the invention. The data segment starting from projection number 17429 shows high values in FIGS. 15b and 15e indicating large motion. The image reconstructed from this data segment shown in FIG. 16a confirms the prediction showing large motion artifacts. On the other hand, the data segment starting at projection number 16763 shows low values in FIGS. 15b and 15e indicating small motion. The image reconstructed from this data segment is illustrated in FIG. 16b showing substantially less motion artifacts making calcification clearly visible.

The reconstructed images indicate a substantial improvement in image quality by successfully removing motion artifacts using the method for tracking motion phase of an object according to the invention.

Figure 17:
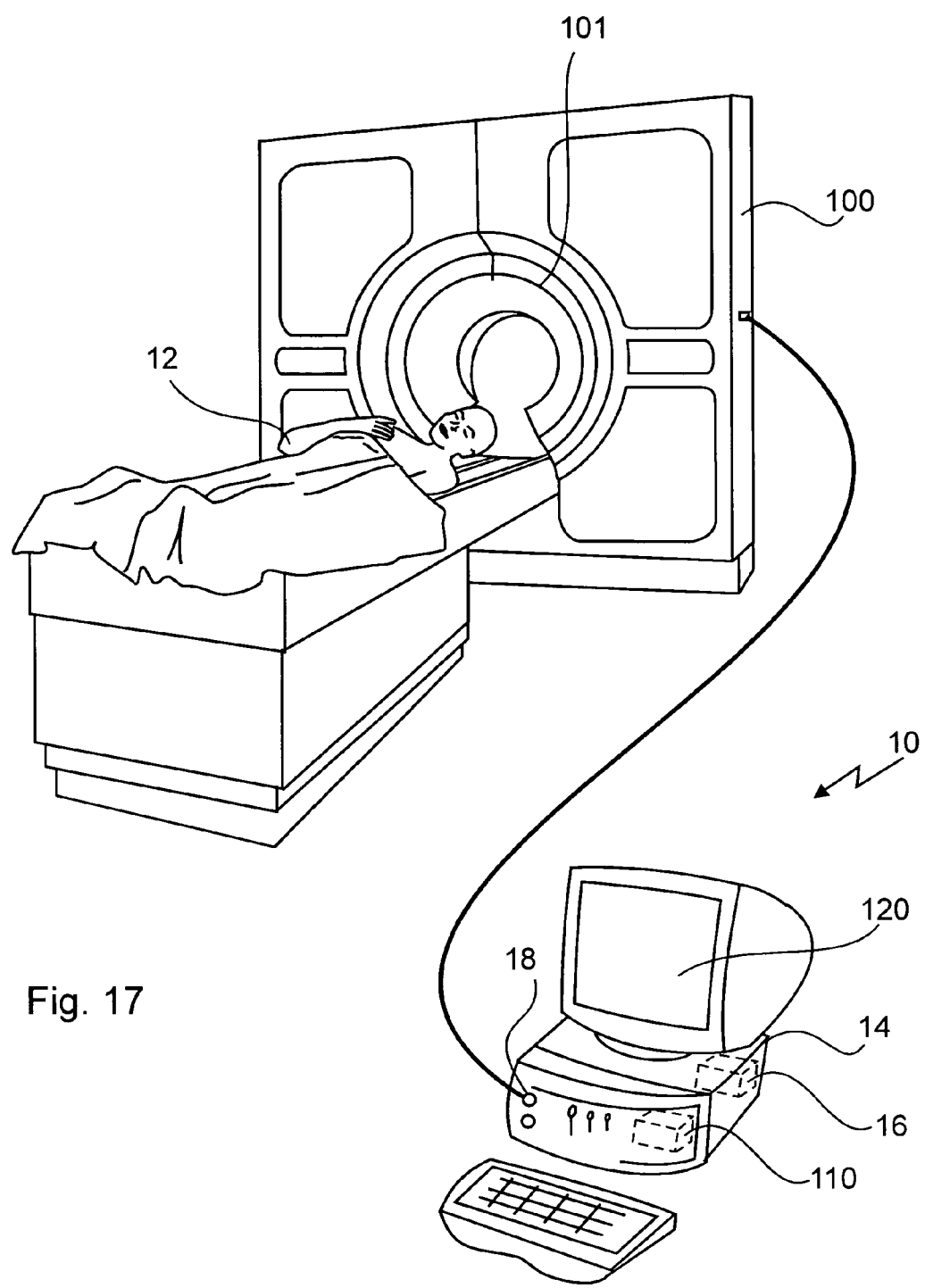
FIG. 17 is a simplified block diagram illustrating a system implementation of the two embodiments of the method for tracking motion phases of an object according to the invention.

Referring to FIG. 17, a system implementation 10 of the two embodiments of the method for tracking motion phase of an object according to the invention is shown. For example, executable commands for execution on a processor 110 of a workstation 14 are stored in non-volatile memory 16. When executing the stored commands the processor 110 performs the processing steps of one of the above embodiments of the method for tracking motion phases of an object. The workstation is linked via port 18 to an X-ray CT scanner 100 for data communication therewith. Projection data acquired from an object 12 are transmitted via port 18 to the workstation 14 for processing. After processing using the method for tracking motion phase of an object, selected projection data are used for reconstructing tomographic images, which are then, for example, provided to a monitor 120 of the workstation 14 for display to a medical practitioner.

Furthermore, it is possible to implement the two embodiments of the method for tracking motion phases of an object according to the invention as retrofit into existing X-ray CT scanners, for example, as executable commands provided on a storage medium for execution on an existing signal processing system.

According to the invention, the two embodiments of the method for tracking motion phase of an object and reconstructing motion artifacts free image are also implementable into the data processing of projection data acquired by multi-slice helical CT scanners, as will be described later. The processing of the projection data comprises two operations: tracking the motion phase and interpolating the missing data. First the operation of interpolation is described. In order to simplify the description, only single-slice helical CT scanner measurements are considered. As will become evident, the same data processing concept is easily extended to process projection data acquired by multi-slice helical CT scanners. The helical CT scan involves a simultaneous translational motion of a patient 12 through gantry 101 along an axis of rotation of an X-ray source and detectors with the X-ray source and the detectors—not shown in FIG. 17—rotating around the patient 12 such that continuous helical projection data are acquired throughout a volume of interest comprising, for example, the patient's heart. The X-ray source and the detectors trace a helical path around the patient while detecting projection data. To obtain a cross-sectional image, the projection data corresponding to a predetermined cross-section—substantially normal to the axis of the translational motion—are determined by interpolating projection data acquired along an axis of the translational motion before and after the predetermined cross-section. Referring to FIG. 18a, a scan diagram for a 360° interpolation process is shown. Slanted lines 200 represent the helical path of the X-ray source and the detectors around the patient's body while it is moved through the gantry with respect to projection angle 202 and the axis of the translational motion 204. For a predetermined cross-section 206 there is only one direct measurement of the projection data available. The other projection data corresponding to the cross-section 206 are obtained by interpolating between projection data that are 360° apart—or the pitch Δz of the helix. These projection data used in the interpolation are acquired from a same projection angle but different axial positions before 208 and after 210 the axial position x of the predetermined cross-section 206. FIG. 18b illustrates the same in a corresponding sinogram of projection data obtained by a plurality of detectors 212 used for the interpolation. In order to generate the projection data of one cross-section 206, i.e. projection data corresponding to one 360° rotation, helical projection data acquired during two complete rotations—or 720°—of the detector array around the patient's body are used. In the case of parallel beam X-ray projection measurements, projection data for only a half rotation—or 180°—of the detector array is sufficient for image reconstruction. However, in order to interpolate the projection data for the cross-section 206 from helical projection data, helical projection data acquired during two complete rotations are utilized. In the case of fan beam X-ray projection measurements, projection data for (180°+fan) angle are used for image reconstruction. Again, helical projection data acquired during two complete rotations are utilized to interpolate the projection data for the cross-section 206.

In the 360° interpolation process the helical projection data acquired span a range of 720°. Interpolation errors are small if the pitch Δz of the helix is relatively small. However, for large pitch, the interpolation errors become more prominent in the reconstructed image. Employment of an 180° interpolation process, shown in FIGS. 19a and 19b, reduces these errors. In this interpolation process the helical projection data used for the interpolation are only 180° apart. According to the symmetry property of the Radon transform, projection data that are acquired 180° apart provide the same line integral along a same physical line through an object and hence are the same. In the case of helical scanning, helical projection data acquired 180° apart have less axial separation compared to helical projection data acquired 360° apart and hence introduce less interpolation errors. In order to generate the projection data of one cross-section 206, helical projection data acquired during one complete rotation—or 360°—of the detector array around the patient's body are used.

Figure 20A:
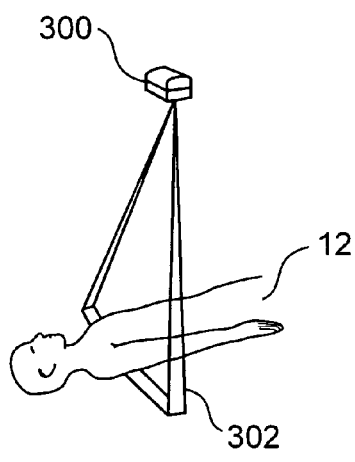
FIGS. 20a and 20b are schematic block diagrams illustrating a single-slice and a multi-slice X-ray CT scanner, respectively.
Figure 20B:
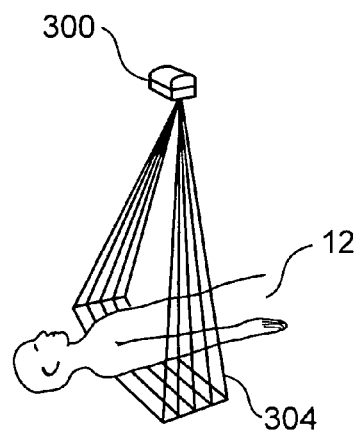

In the following two implementations of the method for tracking motion phase of an object according to the invention for processing helical CT projection data will be disclosed. FIGS. 20a and 20b illustrate data acquisition using a single slice—FIG. 20a—and a multi-slice—FIG. 20b—CT scanner comprising an X-ray source 300 and a single array of detectors 302 or a plurality of detector arrays 304, respectively. In modern multi-slice helical CT scanners, four or more detector arrays are employed. In order to describe the two implementation methods, it is assumed that a distance between two consecutive detector arrays is Δz and the speed of the translational motion of the patient is such that it covers a distance of Δz during one rotation of the detector arrays resulting in an overlap of measurements through each cross-section, i.e. each helical path is traced by each detector array.

Figure 21:
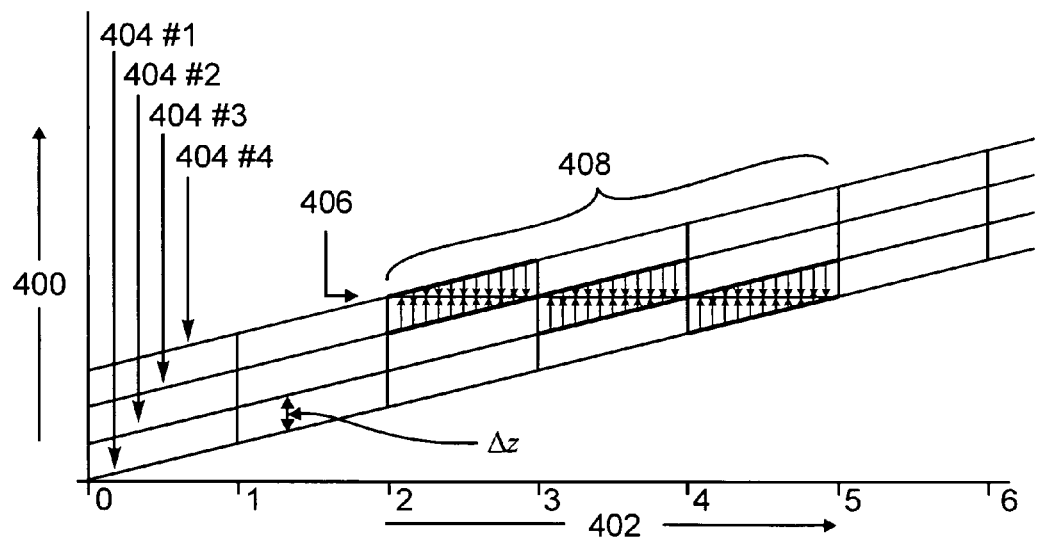
FIG. 21 is a diagram illustrating a first implementation of the method for tracking motion phases of an object with interpolation followed by identification of motion phase.

In a first implementation of the method for tracking motion phase of an object, the interpolation is performed prior motion phase detection. Referring to FIG. 21, acquisition of multi-slice helical projection data is shown as a function of translational movement 400 along a patient and rotation 402 of four detector arrays 404. For a predetermined cross-section 406 helical projection data—indicated by thick lines—that are one rotation on each side of the cross-section 406 are identified for interpolating the projection data of the cross-section 406. It is noted that due to three rotations of the detector arrays 404 and the presence of four detector arrays 404, the acquired helical projection data 408 are equivalent to projection data acquired during twelve rotations of a single-slice CT scanner. Of the helical projection data corresponding to twelve rotations 408, only helical projection data corresponding to six rotations—thick lines—are identified for interpolating the projection data of the cross-section 406. The identified helical projection data is then used in the 360° interpolation process to generate projection data for the cross-section 406. At any given instant, the helical projection data used for interpolating the projection data of the cross-section 406 have been acquired by consecutive detector arrays on either side of the predetermined cross-section 406. These helical projection data have been acquired at a same time instant but at different locations 400. The interpolated projection data of the cross-section 406 is equivalent to projection data generated by a single-slice CT scanner scanning for three rotations in one plane, i.e. the interpolated projection data are equivalent to a sinogram of three rotations. The interpolated projection data are then processed using one of the two embodiments of a method for tracking motion phase of an object to select projection data that have been acquired during, for example, the diastole phase of the cardiac cycle. The selected projection data are then used for reconstructing a tomographic image corresponding to the cross-section 406.

Figure 22:
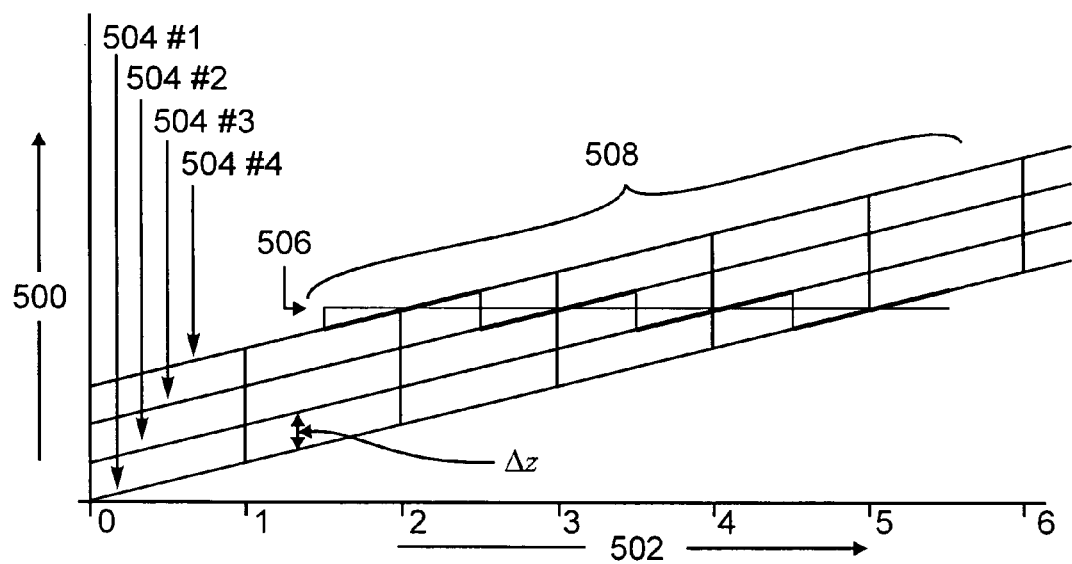
FIG. 22 is a diagram illustrating a second implementation of the method for tracking motion phases of an object with identification of motion followed by interpolation.

In a second implementation of the method for tracking motion phase of an object the interpolation is performed after motion phase detection. Referring to FIG. 22, acquisition of multi-slice helical projection data is shown as a function of translational movement 500 along a patient and rotation 502 of four detector arrays 504. For a predetermined cross-section 506 helical projection data—indicated by thick lines—half a rotation on each side of the cross-section 506 are identified for interpolating the projection data of the cross-section 506. It is noted that due to four rotations of the detector arrays 504 and the presence of four detector arrays 504, the acquired helical projection data 508 is equivalent to projection data acquired during sixteen rotations of a single-slice CT scanner. Of the helical projection data corresponding to sixteen rotations 508 only helical projection data corresponding to four rotations—indicated by thick lines—are identified for interpolating the projection data of the selected cross-section 506. The identified helical projection data are then processed using one of the two embodiments of a method for tracking motion phase of an object to select projection data that have been acquired during a predetermined motion phase, for example, the diastole phase of the cardiac cycle. The helical projection data do not precisely belong to the cross-section 506 but have been acquired in very close proximity. Therefore, it is possible to treat the helical projection data as belonging to the cross-section 506 in the method for tracking a motion phase without introducing substantial errors. After selection of the helical projection data belonging to a predetermined motion phase, the selected helical projection data are used to interpolate projection data belonging to the cross-section 506 using the 180° interpolation process. The interpolated projection data are then used for reconstructing a tomographic image corresponding to the cross-section 506.

In the first implementation—360° interpolation—the multi-slice helical projection data used in the interpolation process have been acquired during two rotations of the detector arrays compared to one rotation in the second implementation—180° interpolation. As a result, the interpolation errors are larger in the first implementation using 360° interpolation. Employing the 360° interpolation, the multi-slice helical projection data used in the interpolation process have been acquired at a same time instance, whereas in the 180° interpolation the multi-slice helical projection data used in the interpolation process have been acquired at different time instances, resulting in some motion artifacts in the reconstructed image for a non-stationary object. Using 180° interpolation helical projection data corresponding to four rotations are available for motion phase identification compared to three rotations when using 360° interpolation. Obviously, a larger amount of projection data has a larger probability of containing a predetermined motion phase.

Alternatively, 360° interpolation is used in the first implementation and 180° interpolation in the second implementation.

Figure 23A:
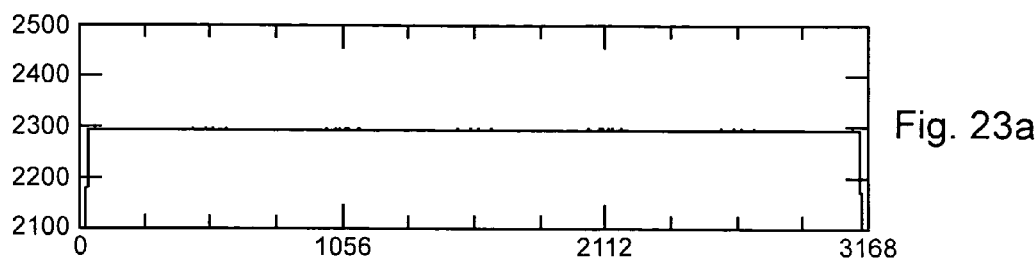
FIGS. 23a to 23d are diagrams illustrating application of the first implementation using Constant Attenuation property of Radon Transform CART for identifying motion phase after 360° interpolation in comparison with the processing of non-helical projection data; and, FIGS. 24a to 24d are diagrams illustrating application of the second implementation using CART for identifying motion phase before 180° interpolation in comparison with the processing of non-helical projection data.
Figure 23B:
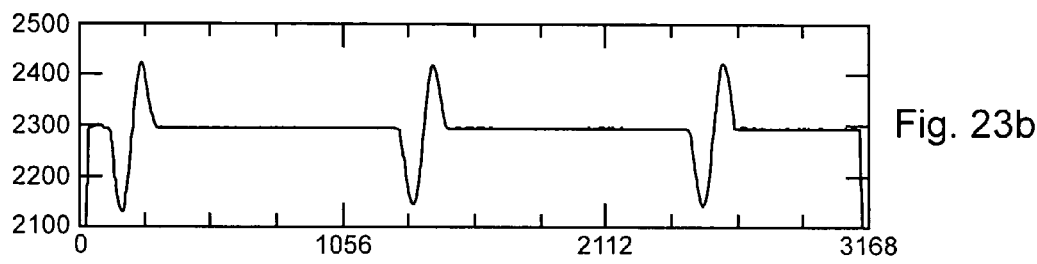
Figure 23C:
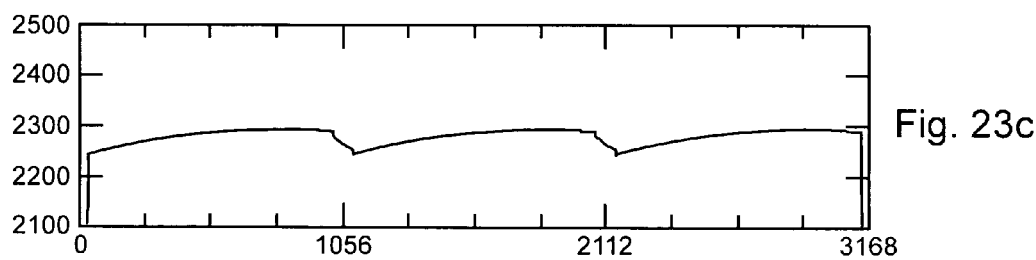
Figure 23D:
Figure 24A:
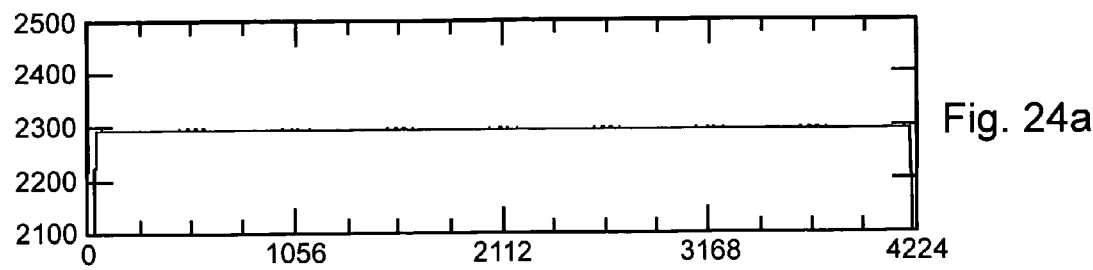
Figure 24B:
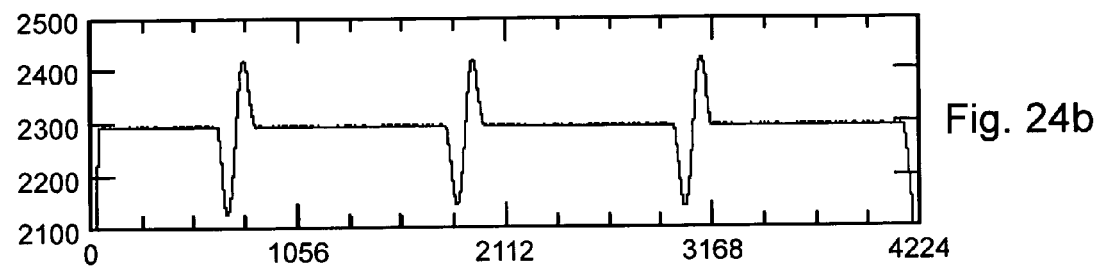
Figure 24C:
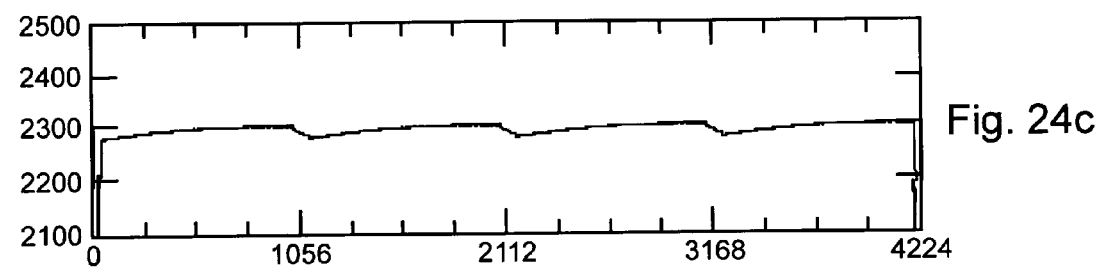
Figure 24D:
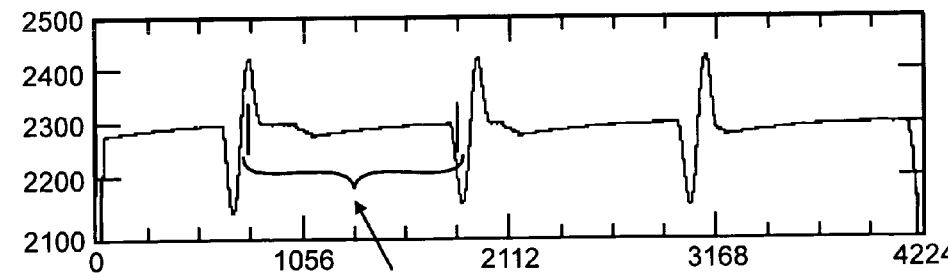

In the following the two implementations outlined above will be compared using simulated projection data for a 3D phantom containing a plurality of ellipsoids. First, non-helical projection data have been generated for a stationary phantom. Employment of the method for tracking motion phase of an object on the simulated projection data for the stationary phantom shows no artifacts, i.e. a non-varying signal, illustrated in FIGS. 23a and 24a. Next, non-helical projection data have been generated for the phantom with one ellipsoid pulsating. Employment of the method for tracking motion phase of an object correctly identifies the pulsating and non-pulsating phases of the phantom, shown in FIGS. 23b and 24b. In a third experiment, helical projection data have been generated for a stationary phantom. FIG. 23c shows a signal obtained after employment of the method for tracking motion phase of an object using the first implementation—360° interpolation followed by motion phase identification. Though the phantom was stationary, the signal after motion identification shows some periodic disturbance with a period equivalent to one rotation, as illustrated in FIG. 23c. A periodic disturbance of the signal—instead of a straight horizontal line as in FIG. 23a—indicates the presence of artifacts due interpolation errors. FIG. 24c illustrates a signal obtained after motion phase identification applied to the identified helical projection data prior the step of interpolation in the second implementation. Again, the signal contains a periodic disturbance indicating the presence of artifacts due to non-planar acquisition of the projection data. A comparison shows that the amplitude of the periodic disturbance in the signal shown in FIG. 24c—second implementation—is smaller than the disturbance in the signal shown in FIG. 23c—first implementation. In a fourth experiment, helical projection data have been generated for the phantom having one ellipsoid pulsating. FIG. 23d illustrates a signal obtained after motion phase identification using the first implementation. The pulsating and non-pulsating phases have been clearly identified. At the same time artifacts due to interpolation errors are visible. A tomographical image reconstructed using projection data corresponding to the interval indicated by an arrow in FIG. 23d will have motion artifacts substantially removed and contain only minor artifacts due to interpolation errors. FIG. 24d illustrates a signal obtained after motion phase identification applied to the identified helical projection data prior interpolation in the second implementation. Again, the pulsating and non-pulsating phases have been clearly identified but artifacts due to non-planar acquisition of the projection data are also visible. Since more projection data are needed for the 180° interpolation in the second implementation than for the 360° interpolation in the first implementation, it was not possible to obtain an interval of contiguous motion free projection data within the duration of a diastole phase—indicated by the arrow in FIG. 24d. As a result, a reconstructed tomographical image will contain some motion artifacts. Artifacts due to non-planar acquisition of the projection data are expected to be insignificant compared to motion artifacts of a non motion corrected image.

Numerous other embodiments of the invention will be apparent to persons skilled in the art without departing from the spirit and scope of the invention as defined in the appended claims.

What is claimed is:

1. A method for tracking motion phase of an object comprising:

receiving a plurality of projection data indicative of at least a cross-sectional image of the object, the projection data being in dependence upon a detector signal indicative of attenuation of an X-ray beam along a line through the object between an X-ray source and a detector, the projection data being acquired such that the projection data are in dependence upon the attenuation along different lines through the object and in dependence upon the attenuation along same lines through the object at different time instances;

processing the projection data for determining motion projection data of the object indicative of motion of the object based on the attenuation along at least a same line through the object at different time instances, the processing comprising:

SOC processing the projection data for removing a signal component in dependence upon stationarity of the object; and, using an unwrapping filter processing the SOC processed projection data for recovering temporal information;

selecting a motion phase of the object from the motion projection data; and, selecting the projection data acquired at time instances within the selected motion phase of the object.

2. A method for tracking motion phase of an object as defined in claim 1 wherein the plurality of projection data are helical projection data and comprising:
   determining a subset of the helical projection data suitable for determining projection data indicative of an image of the object for at least a predetermined cross-section; and,
   determining the projection data indicative of the image of the object for the at least a predetermined cross-section from the subset of the helical projection data using interpolation.

3. A method for tracking motion phase of an object as defined in claim 2 wherein the projection data indicative of the image of the object for the at least a predetermined cross-section are determined before processing the projection data for determining motion projection data of the object indicative of motion of the object.

4. A method for tracking motion phase of an object as defined in claim 2 wherein the projection data indicative of the image of the object for the at least a predetermined cross-section are determined after processing the projection data for determining motion projection data of the object indicative of motion of the object.

5. A method for tracking motion phase of an object as defined in claim 1 wherein the selected motion phase is a motion phase with the object moving the least.

6. A method for tracking motion phase of an object as defined in claim 5 wherein the selected projection data comprise a plurality of portions of consecutively acquired projection data.

7. A method for tracking motion phase of an object as defined in claim 5 comprising reconstructing a tomographic image from the selected projection data.

8. A method for tracking motion phase of an object as defined in claim 1 wherein processing the SOC processed projection data comprises:
   transforming the SOC processed projection data into Fourier domain using FFT, the FFT being applied according to a shift of the projection data in the SOC process;
   processing the transformed SOC processed projection data for determining a signal component in dependence upon motion of the object; and,
   determining motion projection data by transforming the signal component in dependence upon motion of the object into time domain using inverse FFT.

9. A method for tracking motion phase of an object as defined in claim 8 wherein the projection data are shifted equivalent to one rotation of the detector around the object.

10. A method for tracking motion phase of an object as defined in claim 8 wherein the detector comprises a detector array.

11. A method for tracking motion phase of an object as defined in claim 10 comprising adding signals of a plurality of detectors of the detector array for each projection forming a single signal for each projection.

12. A method for tracking motion phase of an object as defined in claim 10 wherein the projection data are processed using symmetry property of a Radon transform of the projection data.

13. A method for tracking motion phase of an object as defined in claim 12 wherein the projection data are shifted equivalent to half a rotation of the deflector array around the object.

14. A method for tracking motion phase of an object as defined in claim 8 comprising sliding window processing of the motion projection data.

15. A method for tracking motion phase of an object comprising:
   receiving a plurality of projection data indicative of at least a cross-sectional image of the object, the projection data being in dependence upon a detector signal indicative of attenuation of an X-ray beam along a line through the object between an X-ray source and a detector, the projection data being acquired such that the projection data are in dependence upon the attenuation along different lines through the object and in dependence upon the attenuation along same lines through the object at different time instances;
   processing the projection data for determining motion projection data of the object indicative of motion of the object based on the attenuation along at least a same line through the object at different time instances, wherein the motion projection data are determined in dependence upon an integral of a Radon transform of the projection data;
   selecting a motion phase of the object from the motion projection data; and
   selecting the projection data acquired at time instances within the selected motion phase of the object.

16. A method for tracking motion phase of an object as defined in claim 15 wherein the detector comprises a detector array.

17. A method for tracking motion phase of an object as defined in claim 16 wherein the integral of the Radon transform is determined from a pN by M sinogram matrix with pN being total number of projections and M being number of detectors in the detector array as sum of the sinogram matrix along M.

18. A method far tracking motion phase of an object as defined in claim 17 wherein the projection data are parallel beam projection data.

19. A method for tracking motion phase of an object as defined in claim 17 wherein the projection data are fan beam projection data.

20. A method for tracking motion phase of an object as defined in claim 19 comprising re-sorting the fan beam projection data into parallel beam projection data.

21. A method for tracking motion phase of an object as defined in claim 15 comprising sliding window processing of the motion projection data.

22. A method for tracking motion phase of an object as defined in claim 15 wherein the plurality of projection data are helical projection data and comprising:
   determining a subset of the helical projection data suitable for determining projection data indicative of an image of the object for at least a predetermined cross-section; and,
   determining the projection data indicative of the image of the object for the at least a predetermined cross-section from the subset of the helical projection data using interpolation.

23. A method for tracking motion phase of an object comprising:
   providing an X-ray source and at least a detector;
   using the at least a detector sensing X-ray beam radiation attenuated by the object along a line trough the object between the X-ray source and the detector and providing projection data in dependence thereupon;
   rotating the X-ray source and the at least a detector around the object for acquiring projection data in dependence upon the attenuation of the X-ray beam along different lines through the object;

rotating the X-ray source and the at least a detector around the object a plurality of times for acquiring projection data in dependence upon the attenuation of the X-ray beam along same lines at different time instances;

processing the projection data for determining motion projection data of the object indicative of motion of the object based on the attenuation along at least a same line through the object at different time instances, the processing comprising:

SOC processing the projection data for removing a signal component in dependence upon stationarity of the object; and, using an unwrapping filter processing the SOC processed projection data for recovering temporal information;

selecting a motion phase of the object from the motion projection data; and, selecting the projection data acquired at time instances within the selected motion phase of the object.

24. A method for tracking motion phase of an object as defined in claim 23 comprising translationally moving the object along an axis of rotation of the X-ray source and the at least a detector.

25. A method for tracking motion phase of an object as defined in claim 24 comprising:

determining a subset of the projection data suitable for determining projection data indicative of an image of the object for at least a predetermined cross-section; and, determining the projection data indicative of the image of the object for the at least a predetermined cross-section from the subset of the projection data using interpolation.

26. A method for tracking motion phase of an object as defined in claim 25 wherein the projection data indicative of the image of the object for the at least a predetermined cross-section are determined before processing the projection data for determining motion projection data of the object indicative of motion of the object.

27. A method for tracking motion phase of an object as defined in claim 25 wherein the projection data indicative of the image of the object for the at least a predetermined cross-section are determined after processing the projection data for determining motion projection data of the object indicative of motion of the object.

28. A method for tracking motion phase of an object as defined in claim 23 wherein processing the SOC processed projection data comprises:

transforming the SOC processed projection data into Fourier domain using FFT, the FFT being applied according to a shift of the projection data in the SOC process;

processing the transformed SOC processed projection data for determining a signal component in dependence upon motion of the object; and, determining motion projection data by transforming the signal component in dependence upon motion of the object into time domain using inverse FFT.

29. A method for tracking motion phase of an object comprising:

providing an X-ray source and at least a detector;

using the at least a detector sensing X-ray beam radiation attenuated by the object along a line through the object between the X-ray source and the detector and providing projection data in dependence thereupon;

rotating the X-ray source and the at least a detector around the object for acquiring projection data in dependence upon the attenuation of the X-ray beam along different lines through the object;

rotating the X-ray source and the at least a detector around the object a plurality of times for acquiring projection data in dependence upon the attenuation of the X-ray beam along same lines at different time instances;

processing the projection data for determining motion projection data of the object indicative of motion of the object based on the attenuation along at least a same line through the object at different time instances, wherein the motion projection data are determined in dependence upon an integral of a Radon transform of the projection data;

selecting a motion phase of the object from the motion projection data; and, selecting the projection data acquired at time instances within the selected motion phase of the object.

30. A method for tracking motion phase of an object as defined in claim 29 comprising translationally moving the object along an axis of rotation of the X-ray source and the at least a detector.

31. A method for tracking motion phase of an object as defined in claim 30 comprising:

determining a subset of the projection data suitable for determining projection data indicative of an image of the object for at least a predetermined cross-section; and, determining the projection data indicative of the image of the object for the at least a predetermined cross-section from the subset of the projection data using interpolation.

32. A storage medium having stored therein data relating to executable commands for execution on a processor, the commands when executed for resulting in:

receiving a plurality of projection data indicative of at least a cross-sectional image of the object, the projection data being in dependence upon a detector signal indicative of attenuation of an X-ray beam along a line through the object between an X-ray source and a detector, the projection data being acquired such that the projection data are in dependence upon the attenuation along different lines through the object and in dependence upon the attenuation along same lines through the object at different time instances;

processing the projection data for determining motion projection data of the object indicative of motion of the object based on the attenuation along at least a same line through the object at different time instances, the processing comprising:

SOC processing the projection data for removing a signal component in dependence upon stationarity of the object; and, using an unwrapping filter processing the SOC processed projection data for recovering temporal information;

selecting a motion phase of the object from the motion projection data; and, selecting the projection data acquired at time instances within the selected motion phase of the object.

33. A storage medium as defined in claim 32 having stored therein data relating to executable commands for execution on a processor, wherein the plurality of projection data are helical projection data, the commands when executed for resulting in:
   determining a subset of the helical projection data suitable for determining projection data indicative of an image of the object for at least a predetermined cross-section; and,
   determining the projection data indicative of the image of the object for the at least a predetermined cross-section from the subset of the projection data using interpolation.

34. A storage medium as defined in claim 32 having stored therein data relating to executable commands for execution on a processor, the commands when executed for resulting in:
   transforming the SOC processed projection data into Fourier domain using FFT, the FFT being applied according to a shift of the projection data in the SOC process;
   processing the transformed SOC processed projection data for determining a signal component in dependence upon motion of the object; and,
   determining motion projection data by transforming the signal component in dependence upon motion of the object into time domain using inverse FFT.

35. A storage medium having stored therein data relating to executable commands for execution on a processor, the commands when executed for resulting in:
   receiving a plurality of projection data indicative of at least a cross-sectional image of the object, the projection data being in dependence upon a detector signal indicative of attenuation of an X-ray beam along a line through the object between an X-ray source and a detector, the projection data being acquired such that the projection data are in dependence upon the attenuation along different lines through the object and in dependence upon the attenuation along same lines through the object at different time instances;
   processing the projection data for determining motion projection data of the object indicative of motion of the object based on the attenuation along at least a same line through the object at different time instances, wherein the motion projection data are determined in dependence upon an integral of a Radon transform of the projection data;
   selecting a motion phase of the object from the motion projection data; and,
   selecting the projection data acquired at time instances within the selected motion phase of the object.

36. A storage medium as defined in claim 35 having stored therein data relating to executable commands for execution on a processor, wherein the plurality of projection data are helical projection data, the commands when executed for resulting in:
   determining a subset of the helical projection data suitable for determining projection data indicative of an image of the object for at least a predetermined cross-section; and,
   determining the projection data indicative of the image of the object for the at least a predetermined cross-section from the subset of the projection data using interpolation.

* * * * *